(12) United States Patent
Hart

(10) Patent No.: US 6,432,666 B1
(45) Date of Patent: *Aug. 13, 2002

(54) DENDRITIC CELL RECEPTOR

(75) Inventor: Derek N. Hart, Christchurch (NZ)

(73) Assignee: The Corporation of the Trustees of the Sisters of Mercy in Queensland, Queensland (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/194,612

(22) PCT Filed: May 29, 1997

(86) PCT No.: PCT/NZ97/00068

§ 371 (c)(1),
(2), (4) Date: Mar. 18, 1999

(87) PCT Pub. No.: WO97/45449

PCT Pub. Date: Dec. 4, 1997

(30) Foreign Application Priority Data

May 29, 1996 (NZ) .................................. 286692

(51) Int. Cl.7 ............................. C12N 5/10; C12N 5/12; C07K 14/47
(52) U.S. Cl. .................... 435/69.1; 435/70.1; 435/71.1; 435/471; 435/325; 435/252.3; 435/320; 536/23.1; 536/23.5; 530/350
(58) Field of Search ................................ 435/69.1, 70.1, 435/71.1, 471, 325, 252.3, 320; 536/23.1, 23.5; 530/350

(56) References Cited

FOREIGN PATENT DOCUMENTS

WO      96/23882      8/1996

OTHER PUBLICATIONS

Cellular Immunology (1195) vol. 165, pp. 302–311 by Swiggard WJ et al. "DEC–205, a 205–kDa protein abundant on mouse dendritic cells and thymic epithelium that is detected by the monoclonal antibody NLDC–145; Purification, characterisation and N–terminal amino acid sequence" See the entire document.

Swiggard et al, "DEC–205, a 205–kDa Protein Abundant . . .," Cellular Immunology, vol. 165, pp. 302–311 (1995).

*Primary Examiner*—Yvonne Eyler
*Assistant Examiner*—Fozia Hamud
(74) *Attorney, Agent, or Firm*—Nixon & Vanderhye

(57) ABSTRACT

An isolated human dendritic cell receptor comprising amino acid sequences selected from: TVDCNDNQPGAICYYS-GNETEKEVKPVDSVKCPSPVLNTPWIPFQNCCYN FIITKNRHMATTQDEVQSTCEKLHPK-SHILSIRDEKENNFVLEQLLYFNYMA SWVMLGI-TYRNNSL amino acid at position 1208–1323 of SEQ ID NO:1 and SQHRLFHLHSQKCLGLDITKSVNELRMF-SCDSSAML amino acid at position 71–106 of SEQ ID NO:1.

6 Claims, 15 Drawing Sheets

DEC-205 DNA sequence (coding region only)

```
   1 ATGAGGACAG GCTGGGCGCA CCCCTCGCCG CCCGGCGGGG CTCCTCATGC
  51 TGCTCTTCTG GTTCTTCGAT CTCGCGGAGC CCTCTGGCCG CGCACTAATG
 101 ACCCCTTCAC CATCGTCCAT GGAAATACGG GCAAGTGCAT CAAGCCAGTG
 151 TATGGCTGGA TAGTAGCAGA CGACTGTGAT GAAACTGAGG ACAAGTTATG
 201 GAAGTGGGTG TCCCAGCATC GGCTCTTTCA TTTGCACTCC CAAAAGTGCC
 251 TTGGCCTCGA TATTACCAAA TCGGTAAATG AGCTGAGAAT GTTCAGCTGT
 301 GACTCCAGTG CCATGCTGTG GTGGAAATGT GAGCACCACT CTCTGTACGG
 351 AGCTGCCCGG TACTGGCTGG CTCTGAAGGA TGGACATGGC ACAGCAATCT
 401 CAAATGCATC TGATGTCTGG AAGAAAGGAG GCTCAGAGGA AAGCCTTTGT
 451 GACCAGCCTT ATCATGAGAT CTATACCAGA GATGGGAACT CTTATGGGAG
 501 ACCTTGTGAA TTTCCATTCT TAATTGATGG GACCTGGCAT CATGATTGCA
 551 TTCTTGATGA AGATCATAGT GGGCCATGGT GTGCCACCAC CTTAAATTAT
 601 GAATATGACC GAAAGTGGGG CATCTGCTTA AAGCCTGAAA ACGGTTGTGA
 651 AGATAATTGG GAAAAGAACG AGCAGTTTGG AAGTTGCTAC CAATTTAATA
 701 CTCAGACGGC TCTTTCTTGG AAAGAAGCTT ATGTTTCATG TCAGAATCAA
 751 GGAGCTGATT TACTGAGCAT CAACAGTGCT GCTGAATTAA CTTACCTTAA
 801 AGAAAAAGAA GGCATTGCTA AGATTTTCTG GATTGGTTTA AATCAGCTAT
 851 ACTCTGCTAG AGGCTGGGAA TGGTCAGACC ACAAACCATT AAACTTTCTC
 901 AACTGGGATC CAGACAGGCC CAGTGCACCT ACTATAGGTG GCTCCAGCTG
 951 TGCAAGAATG GATGCTGAGT CTGGTCTGTG GCAGAGCTTT TCCTGTGAAG
1001 CTCAACTGCC CTATGTCTGC AGGAAACCAT TAAATAATAC AGTGGAGTTA
1051 ACAGATGTCT GGACATACTC AGATACCCGC TGTGATGCAG GCTGGCTGCC
1101 AAATAATGGA TTTTGCTATC TGCTGGTAAA TGAAAGTAAT TCCTGGGATA
1151 AGGCACATGC GAAATGCAAA GCCTTCAGTA GTGACCTAAT CAGCATTCAT
1201 TCTCTAGCAG ATGTGGAGGT GGTTGTCACA AAACTCCATA ATGAGGATAT
1251 CAAAGAAGAA GTGTGGATAG GCCTTAAGAA CATAAACATA CCAACTTTAT
```

Figure 10

1301 TTCAGTGGTC AGATGGTACT GAAGTTACTC TAACATATTG GGATGAGAAT

1351 GAGCCAAATG TTCCCTACAA TAAGACGCCC AACTGTGTTT CCTACTTAGG

1401 AGAGCTAGGT CAGTGGAAAG TCCAATCATG TGAGGAGAAA CTAAAATATG

1451 TATGCAAGAG AAAGGGAGAA AAACTGAATG ACGCAAGTTC TGATAAGATG

1501 TGTCCTCCAG ATGAGGGCTG GAAGAGACAT GGAGAAACCT GTTACAAGAT

1551 TTATGAGGAT GAGGTCCCTT TTGGAACAAA CTGCAATCTG ACTATCACTA

1601 GCAGATTTGA GCAAGAATAC CTAAATGATT TGATGAAAAA GTATGATAAA

1651 TCTCTAAGAA AATACTTCTG GACTGGCCTG AGAGATGTAG ATTCTTGTGG

1701 AGAGTATAAC TGGGCAACTG TTGGTGGAAG AAGGCGGGCT GTAACCTTTT

1751 CCAACTGGAA TTTTCTTGAG CCAGCTTCCC CGGGCGGCTG CGTGGCTATG

1801 TCTACTGGAA AGTCTGTTGG AAAGTGGGAG GTGAAGGACT GCAGAAGCTT

1851 CAAAGCACTT TCAATTTGCA AGAAAATGAG TGGACCCCTT GGGCCTGAAG

1901 AAGCATCCCC TAAGCCTGAT GACCCTGTC CTGAAGGCTG GCAGAGTTTC

1951 CCCGCAAGTC TTTCTTGTTA TAAGGTATTC CATGCAGAAA GAATTGTAAG

2001 AAAGAGGAAC TGGGAAGAAG CTGAACGATT CTGCCAAGCC CTTGGAGCAC

2051 ACCTTTCTAG CTTCAGCCAT GTGGATGAAA TAAAGGAATT TCTTCACTTT

2101 TTAACGGACC AGTTCAGTGG CCAGCATTGG CTGTGGATTG GTTTGAATAA

2151 AAGGAGCCCA GATTTACAAG GATCCTGGCA ATGGAGTGAT CGTACACCAG

2201 TGTCTACTAT TATCATGCCA AATGAGTTTC AGCAGGATTA TGACATCAGA

2251 GACTGTGCTG CTGTCAAGGT ATTTCATAGG CCATGGCGAA GAGGCTGGCA

2301 TTTCTATGAT GATAGAGAAT TTATTTATTT GAGGCCTTTT GCTTGTGATA

2351 CAAAACTTGA ATGGGTGTGC CAAATTCCAA AAGGCCGTAC TCCAAAAACA

2401 CCAGACTGGT ACAATCCAGA CCGTGCTGGA ATTCATGGAC CTCCACTTAT

2451 AATTGAAGGA AGTGAATATT GGTTTGTTGC TGATCTTCAC CTAAACTATG

2501 AAGAAGCCGT CCTGTACTGT GCCAGCAATC ACAGCTTTCT TGCGACTATA

2551 ACATCTTTTG TGGGACTAAA AGCCATCAAA AACAAAATAG CAAATATATC

2601 TGGTGATGGA CAGAAGTGGT GGATAAGAAT TAGCGAGTGG CCAATAGATG

Figure 10A

2651 ATCATTTTAC ATACTCACGA TATCCATGGC ACCGCTTTCC TGTGACATTT

2701 GGAGAGGAAT GCTTGTACAT GTCTGCCAAG ACTTGGCTTA TCGACTTAGG

2751 TAAACCAACA GACTGTAGTA CCAAGTTGCC CTTCATCTGT GAAAAATATA

2801 ATGTTTCTTC GTTAGAGAAA TACAGCCCAG ATTCTGCAGC TAAAGTGCAA

2851 TGTTCTGAGC AATGGATTCC TTTTCAGAAT AAGTGTTTTC TAAAGATCAA

2901 ACCCGTGTCT CTCACATTTT CTCAAGCAAG CGATACCTGT CACTCCTATG

2951 GTGGCACCCT TCCTTCAGTG TTGAGCCAGA TTGAACAAGA CTTTATTACA

3001 TCCTTGCTTC CGGATATGGA AGCTACTTTA TGGATTGGTT TGCGCTGGAC

3051 TGCCTATGAA AAGATAAACA AATGGACAGA TAACAGAGAG CTGACGTACA

3101 GTAACTTTCA CCCATTATTG GTTAGTGGGA GGCTGAGAAT ACCAGAAAAT

3151 TTTTTTGAGG AAGAGTCTCG CTACCACTGT GCCCTAATAC TCAACCTCCA

3201 AAAATCACCG TTTACTGGGA CGTGGAATTT TACATCCTGC AGTGAACGCC

3251 ACTTTGTGTC TCTCTGTCAG AAATATTCAG AAGTTAAAAG CAGACAGACG

3301 TTGCAGAATG CTTCAGAAAC TGTAAAGTAT CTAAATAATC TGTACAAAAT

3351 AATCCCAAAG ACTCTGACTT GGCACAGTGC TAAAAGGGAG TGTCTGAAAA

3401 GTAACATGCA GCTGGTGAGC ATCACGGACC CTTACCAGCA GGCATTCCTC

3451 AGTGTGCAGG CGCTCCTTCA CAACTCTTCC TTATGGATCG GACTCTTCAG

3501 TCAAGATGAT GAACTCAACT TTGGTTGGTC AGATGGGAAA CGTCTTCATT

3551 TTAGTCGCTG GGCTGAAACT AATGGGCAAC TCGAAGACTG TGTAGTATTA

3601 GACACTGATG GATTCTGGAA AACAGTTGAT TGCAATGACA ATCAACCAGG

3651 TGCTATTTGC TACTATTCAG GAAATGAGAC TGAAAAAGAG GTCAAACCAG

3701 TTGACAGTGT TAAATGTCCA TCTCCTGTTC TAAATACTCC GTGGATACCA

3751 TTTCAGAACT GTTGCTACAA TTTCATAATA ACAAAGAATA GGCATATGGC

3801 AACAACACAG GATGAAGTTC ATACTAAATG CCAGAAACTG AATCCAAAAT

3851 CACATATTCT GAGTATTCGA GATGAAAAGG AGAATAACTT TGTTCTTGAG

3901 CAACTGCTGT ACTTCAATTA TATGGCTTCA TGGGTCATGT TAGGAATAAC

3951 TTATAGAAAT AATTCTCTTA TGTGGTTTGA TAAGACCCCA CTGTCATATA

Figure 10B

```
4001 CACATTGGAG AGCAGGAAGA CCAACTATAA AAAATGAGAA GTTTTTGGCT

4051 GGTTTAAGTA CTGACGGCTT CTGGGATATT CAAACCTTTA AAGTTATTGA

4101 AGAAGCAGTT TATTTTCACC AGCACAGCAT TCTTGCTTGT AAAATTGAAA

4151 TGGTTGACTA CAAAGAAGAA CATAATACTA CACTGCCACA GTTTATGCCA

4201 TATGAAGATG GTATTTACAG TGTTATTCAA AAAAAGGTAA CATGGTATGA

4251 AGCATTAAAC ATGTGTTCTC AAAGTGGAGG TCACTTGGCA AGCGTTCACA

4301 ACCAAAATGG CCAGCTCTTT CTGGAAGATA TTGTAAAACG TGATGGATTT

4351 CCACTATGGG TTGGGCTCTC AAGTCATGAT GGAAGTGAAT CAAGTTTTGA

4401 ATGGTCTGAT GGTAGTACAT TTGACTATAT CCCATGGAAA GGCCAAACAT

4451 CTCCTGGAAA TTGTGTTCTC TTGGATCCAA AAGGAACTTG GAAACATGAA

4501 AAATGCAACT CTGTTAAGGA TGGTGCTATT TGTTATAAAC CTACAAAATC

4551 TAAAAAGCTG TCCCGTCTTA CATATTCATC AAGATGTCCA GCAGCAAAAG

4601 AGAATGGGTC ACGGTGGATC CAGTACAAGG GTCACTGTTA CAAGTCTGAT

4651 CAGGCATTGC ACAGTTTTTC AGAGGCCAAA AAATTGTGTT CAAAACATGA

4701 TCACTCTGCA ACTATCGTTT CCATAAAAGA TGAAGATGAG AATAAATTTG

4751 TGAGCAGACT GATGAGGGAA AATAATAACA TTACCATGAG AGTTTGGCTT

4801 GGATTATCTC AACATTCTGT TGACCAGTCT TGGAGTTGGT TAGATGGATC

4851 AGAAGTGACA TTTGTCAAAT GGGAAAATAA AAGTAAGAGT GGTGTTGGAA

4901 GATGTAGCAT GTTGATAGCT TCAAATGAAA CTTGGAAAAA AGTTGAATGT

4951 GAACATGGTT TTGGAAGAGT TGTCTGCAAA GTGCCTCTGG GCCCTGATTA

5001 CACAGCAATA GCTATCATAG TTGCCACACT AAGTATCTTA GTTCTCATGG

5051 GCGGACTGAT TTGGTTCCTC TTCCAAAGGC ACCGTTTGCA CCTGGCGGGT

5101 TTCTCATCAG TTCGATATGC ACAAGGAGTG AATGAAGATG AGATTATGCT

5151 TCCTTCTTTC CATGAC
```

Figure 10C

DEC-205 protein sequence

1 MRTGWAHPSP PGGAPHAALL VLRSRGALWP RTNDPFTIVH GNTGKCIKPV

51 YGWIVADDCD ETEDKLWKWV SQHRLFHLHS QKCLGLDITK SVNELRMFSC

101 DSSAMLWWKC EHHSLYGAAR YWLALKDGHG TAISNASDVW KKGGSEESLC

151 DQPYHEIYTR DGNSYGRPCE FPFLIDGTWH HDCILDEDHS GPWCATTLNY

201 EYDRKWGICL KPENGCEDNW EKNEQFGSCY QFNTQTALSW KEAYVSCQNQ

251 GADLLSINSA AELTYLKEKE GIAKIFWIGL NQLYSARGWE WSDHKPLNFL

301 NWDPDRPSAP TIGGSSCARM DAESGLWQSF SCEAQLPYVC RKPLNNTVEL

351 TDVWTYSDTR CDAGWLPNNG FCYLLVNESN SWDKAHAKCK AFSSDLISIH

401 SLADVEVVVT KLHNEDIKEE VWIGLKNINI PTLFQWSDGT EVTLTYWDEN

451 EPNVPYNKTP NCVSYLGELG QWKVQSCEEK LKYVCKRKGE KLNDASSDKM

501 CPPDEGWKRH GETCYKIYED EVPFGTNCNL TITSRFEQEY LNDLMKKYDK

551 SLRKYFWTGL RDVDSCGEYN WATVGGRRRA VTFSNWNFLE PASPGGCVAM

601 STGKSVGKWE VKDCRSFKAL SICKKMSGPL GPEEASPKPD DPCPEGWQSF

651 PASLSCYKVF HAERIVRKRN WEEAERFCQA LGAHLSSFSH VDEIKEFLHF

701 LTDQFSGQHW LWIGLNKRSP DLQGSWQWSD RTPVSTIIMP NEFQQDYDIR

751 DCAAVKVFHR PWRRGWHFYD DREFIYLRPF ACDTKLEWVC QIPKGRTPKT

801 PDWYNPDRAG IHGPPLIIEG SEYWFVADLH LNYEEAVLYC ASNHSFLATI

851 TSFVGLKAIK NKIANISGDG QKWWIRISEW PIDDHFTYSR YPWHRFPVTF

901 GEECLYMSAK TWLIDLGKPT DCSTKLPFIC EKYNVSSLEK YSPDSAAKVQ

951 CSEQWIPFQN KCFLKIKPVS LTFSQASDTC HSYGGTLPSV LSQIEQDFIT

1001 SLLPDMEATL WIGLRWTAYE KINKWTDNRE LTYSNFHPLL VSGRLRIPEN

1051 FFEEESRYHC ALILNLQKSP FTGTWNFTSC SERHFVSLCQ KYSEVKSRQT

1101 LQNASETVKY LNNLYKIIPK TLTWHSAKRE CLKSNMQLVS ITDPYQQAFL

1151 SVQALLHNSS LWIGLFSQDD ELNFGWSDGK RLHFSRWAET NGQLEDCVVL

1201 DTDGFWKTVD CNDNQPGAIC YYSGNETEKE VKPVDSVKCP SPVLNTPWIP

1251 FQNCCYNFII TKNRHMATTQ DEVHTKCQKL NPKSHILSIR DEKENNFVLE

Figure 11

1301 QLLYFNYMAS WVMLGITYRN NSLMWFDKTP LSYTHWRAGR PTIKNEKFLA

1351 GLSTDGFWDI QTFKVIEEAV YFHQHSILAC KIEMVDYKEE HNTTLPQFMP

1401 YEDGIYSVIQ KKVTWYEALN MCSQSGGHLA SVHNQNGQLF LEDIVKRDGF

1451 PLWVGLSSHD GSESSFEWSD GSTFDYIPWK GQTSPGNCVL LDPKGTWKHE

1501 KCNSVKDGAI CYKPTKSKKL SRLTYSSRCP AAKENGSRWI QYKGHCYKSD

1551 QALHSFSEAK KLCSKHDHSA TIVSIKDEDE NKFVSRLMRE NNNITMRVWL

1601 GLSQHSVDQS WSWLDGSEVT FVKWENKSKS GVGRCSMLIA SNETWKKVEC

1651 EHGFGRVVCK VPLGPDYTAI AIIVATLSIL VLMGGLIWFL FQRHRLHLAG

1701 FSSVRYAQGV NEDEIMLPSF HD*

Figure 11A

SEQUENCE LISTING

<160> NUMBER OF SEQ ID NOS: 31

<210> SEQ ID NO 1
<211> LENGTH: 1722
<212> TYPE: PRT
<213> ORGANISM: Homo sapiens

<400> SEQUENCE: 1

```
Met Arg Thr Gly Trp Ala His Pro Ser Pro Pro Gly Gly Ala Pro His
 1               5                  10                  15

Ala Ala Leu Leu Val Leu Arg Ser Arg Gly Ala Leu Trp Pro Arg Thr
            20                  25                  30

Asn Asp Pro Phe Thr Ile Val His Gly Asn Thr Gly Lys Cys Ile Lys
        35                  40                  45

Pro Val Tyr Gly Trp Ile Val Ala Asp Asp Cys Asp Glu Thr Glu Asp
    50                  55                  60

Lys Leu Trp Lys Trp Val Ser Gln His Arg Leu Phe His Leu His Ser
65                  70                  75                  80

Gln Lys Cys Leu Gly Leu Asp Ile Thr Lys Ser Val Asn Glu Leu Arg
                85                  90                  95

Met Phe Ser Cys Asp Ser Ser Ala Met Leu Trp Trp Lys Cys Glu His
            100                 105                 110

His Ser Leu Tyr Gly Ala Ala Arg Tyr Trp Leu Ala Leu Lys Asp Gly
        115                 120                 125
```

```
His Gly Thr Ala Ile Ser Asn Ala Ser Asp Val Trp Lys Lys Gly Gly
    130                 135                 140

Ser Glu Glu Ser Leu Cys Asp Gln Pro Tyr His Glu Ile Tyr Thr Arg
145                 150                 155                 160

Asp Gly Asn Ser Tyr Gly Arg Pro Cys Glu Phe Pro Phe Leu Ile Asp
                165                 170                 175

Gly Thr Trp His His Asp Cys Ile Leu Asp Glu Asp His Ser Gly Pro
            180                 185                 190

Trp Cys Ala Thr Thr Leu Asn Tyr Glu Tyr Asp Arg Lys Trp Gly Ile
        195                 200                 205

Cys Leu Lys Pro Glu Asn Gly Cys Glu Asp Asn Trp Glu Lys Asn Glu
    210                 215                 220

Gln Phe Gly Ser Cys Tyr Gln Phe Asn Thr Gln Thr Ala Leu Ser Trp
225                 230                 235                 240

Lys Glu Ala Tyr Val Ser Cys Gln Asn Gln Gly Ala Asp Leu Leu Ser
                245                 250                 255

Ile Asn Ser Ala Ala Glu Leu Thr Tyr Leu Lys Glu Lys Glu Gly Ile
            260                 265                 270

Ala Lys Ile Phe Trp Ile Gly Leu Asn Gln Leu Tyr Ser Ala Arg Gly
        275                 280                 285

Trp Glu Trp Ser Asp His Lys Pro Leu Asn Phe Leu Asn Trp Asp Pro
    290                 295                 300

Asp Arg Pro Ser Ala Pro Thr Ile Gly Gly Ser Ser Cys Ala Arg Met
305                 310                 315                 320

Asp Ala Glu Ser Gly Leu Trp Gln Ser Phe Ser Cys Glu Ala Gln Leu
                325                 330                 335

Pro Tyr Val Cys Arg Lys Pro Leu Asn Asn Thr Val Glu Leu Thr Asp
            340                 345                 350

Val Trp Thr Tyr Ser Asp Thr Arg Cys Asp Ala Gly Trp Leu Pro Asn
        355                 360                 365

Asn Gly Phe Cys Tyr Leu Leu Val Asn Glu Ser Asn Ser Trp Asp Lys
    370                 375                 380

Ala His Ala Lys Cys Lys Ala Phe Ser Ser Asp Leu Ile Ser Ile His
385                 390                 395                 400

Ser Leu Ala Asp Val Glu Val Val Thr Lys Leu His Asn Glu Asp
                405                 410                 415

Ile Lys Glu Glu Val Trp Ile Gly Leu Lys Asn Ile Asn Ile Pro Thr
            420                 425                 430

Leu Phe Gln Trp Ser Asp Gly Thr Glu Val Thr Leu Thr Tyr Trp Asp
        435                 440                 445

Glu Asn Glu Pro Asn Val Pro Tyr Asn Lys Thr Pro Asn Cys Val Ser
    450                 455                 460

Tyr Leu Gly Glu Leu Gly Gln Trp Lys Val Gln Ser Cys Glu Glu Lys
465                 470                 475                 480

Leu Lys Tyr Val Cys Lys Arg Lys Gly Glu Lys Leu Asn Asp Ala Ser
                485                 490                 495

Ser Asp Lys Met Cys Pro Pro Asp Glu Gly Trp Lys Arg His Gly Glu
            500                 505                 510

Thr Cys Tyr Lys Ile Tyr Glu Asp Glu Val Pro Phe Gly Thr Asn Cys
        515                 520                 525

Asn Leu Thr Ile Thr Ser Arg Phe Glu Gln Glu Tyr Leu Asn Asp Leu
    530                 535                 540
```

-continued

```
Met Lys Lys Tyr Asp Lys Ser Leu Arg Lys Tyr Phe Trp Thr Gly Leu
545                 550                 555                 560

Arg Asp Val Asp Ser Cys Gly Glu Tyr Asn Trp Ala Thr Val Gly Gly
            565                 570                 575

Arg Arg Arg Ala Val Thr Phe Ser Asn Trp Asn Phe Leu Glu Pro Ala
        580                 585                 590

Ser Pro Gly Gly Cys Val Ala Met Ser Thr Gly Lys Ser Val Gly Lys
    595                 600                 605

Trp Glu Val Lys Asp Cys Arg Ser Phe Lys Ala Leu Ser Ile Cys Lys
        610                 615                 620

Lys Met Ser Gly Pro Leu Gly Pro Glu Glu Ala Ser Pro Lys Pro Asp
625                 630                 635                 640

Asp Pro Cys Pro Glu Gly Trp Gln Ser Phe Pro Ala Ser Leu Ser Cys
            645                 650                 655

Tyr Lys Val Phe His Ala Glu Arg Ile Val Arg Lys Arg Asn Trp Glu
            660                 665                 670

Glu Ala Glu Arg Phe Cys Gln Ala Leu Gly Ala His Leu Ser Ser Phe
        675                 680                 685

Ser His Val Asp Glu Ile Lys Glu Phe Leu His Phe Leu Thr Asp Gln
    690                 695                 700

Phe Ser Gly Gln His Trp Leu Trp Ile Gly Leu Asn Lys Arg Ser Pro
705                 710                 715                 720

Asp Leu Gln Gly Ser Trp Gln Trp Ser Asp Arg Thr Pro Val Ser Thr
            725                 730                 735

Ile Ile Met Pro Asn Glu Phe Gln Gln Asp Tyr Asp Ile Arg Asp Cys
            740                 745                 750

Ala Ala Val Lys Val Phe His Arg Pro Trp Arg Arg Gly Trp His Phe
        755                 760                 765

Tyr Asp Asp Arg Glu Phe Ile Tyr Leu Arg Pro Phe Ala Cys Asp Thr
    770                 775                 780

Lys Leu Glu Trp Val Cys Gln Ile Pro Lys Gly Arg Thr Pro Lys Thr
785                 790                 795                 800

Pro Asp Trp Tyr Asn Pro Asp Arg Ala Gly Ile His Gly Pro Pro Leu
            805                 810                 815

Ile Ile Glu Gly Ser Glu Tyr Trp Phe Val Ala Asp Leu His Leu Asn
            820                 825                 830

Tyr Glu Glu Ala Val Leu Tyr Cys Ala Ser Asn His Ser Phe Leu Ala
        835                 840                 845

Thr Ile Thr Ser Phe Val Gly Leu Lys Ala Ile Lys Asn Lys Ile Ala
    850                 855                 860

Asn Ile Ser Gly Asp Gly Gln Lys Trp Trp Ile Arg Ile Ser Glu Trp
865                 870                 875                 880

Pro Ile Asp Asp His Phe Thr Tyr Ser Arg Tyr Pro Trp His Arg Phe
            885                 890                 895

Pro Val Thr Phe Gly Glu Glu Cys Leu Tyr Met Ser Ala Lys Thr Trp
            900                 905                 910

Leu Ile Asp Leu Gly Lys Pro Thr Asp Cys Ser Thr Lys Leu Pro Phe
        915                 920                 925

Ile Cys Glu Lys Tyr Asn Val Ser Ser Leu Glu Lys Tyr Ser Pro Asp
    930                 935                 940

Ser Ala Ala Lys Val Gln Cys Ser Glu Gln Trp Ile Pro Phe Gln Asn
945                 950                 955                 960

Lys Cys Phe Leu Lys Ile Lys Pro Val Ser Leu Thr Phe Ser Gln Ala
```

-continued

```
                965               970                975
Ser Asp Thr Cys His Ser Tyr Gly Gly Thr Leu Pro Ser Val Leu Ser
                    980              985                990

Gln Ile Glu Gln Asp Phe Ile Thr Ser Leu Leu Pro Asp Met Glu Ala
         995              1000             1005

Thr Leu Trp Ile Gly Leu Arg Trp Thr Ala Tyr Glu Lys Ile Asn Lys
    1010             1015            1020

Trp Thr Asp Asn Arg Glu Leu Thr Tyr Ser Asn Phe His Pro Leu Leu
1025             1030            1035            1040

Val Ser Gly Arg Leu Arg Ile Pro Glu Asn Phe Phe Glu Glu Ser
             1045            1050            1055

Arg Tyr His Cys Ala Leu Ile Leu Asn Leu Gln Lys Ser Pro Phe Thr
            1060            1065            1070

Gly Thr Trp Asn Phe Thr Ser Cys Ser Glu Arg His Phe Val Ser Leu
        1075            1080            1085

Cys Gln Lys Tyr Ser Glu Val Lys Ser Arg Gln Thr Leu Gln Asn Ala
    1090            1095            1100

Ser Glu Thr Val Lys Tyr Leu Asn Asn Leu Tyr Lys Ile Ile Pro Lys
1105            1110            1115            1120

Thr Leu Thr Trp His Ser Ala Lys Arg Glu Cys Leu Lys Ser Asn Met
            1125            1130            1135

Gln Leu Val Ser Ile Thr Asp Pro Tyr Gln Gln Ala Phe Leu Ser Val
        1140            1145            1150

Gln Ala Leu Leu His Asn Ser Ser Leu Trp Ile Gly Leu Phe Ser Gln
        1155            1160            1165

Asp Asp Glu Leu Asn Phe Gly Trp Ser Asp Gly Lys Arg Leu His Phe
    1170            1175            1180

Ser Arg Trp Ala Glu Thr Asn Gly Gln Leu Glu Asp Cys Val Val Leu
1185            1190            1195            1200

Asp Thr Asp Gly Phe Trp Lys Thr Val Asp Cys Asn Asp Asn Gln Pro
            1205            1210            1215

Gly Ala Ile Cys Tyr Tyr Ser Gly Asn Glu Thr Glu Lys Glu Val Lys
            1220            1225            1230

Pro Val Asp Ser Val Lys Cys Pro Ser Pro Val Leu Asn Thr Pro Trp
    1235            1240            1245

Ile Pro Phe Gln Asn Cys Cys Tyr Asn Phe Ile Ile Thr Lys Asn Arg
    1250            1255            1260

His Met Ala Thr Thr Gln Asp Glu Val His Thr Lys Cys Gln Lys Leu
1265            1270            1275            1280

Asn Pro Lys Ser His Ile Leu Ser Ile Arg Asp Glu Lys Glu Asn Asn
            1285            1290            1295

Phe Val Leu Glu Gln Leu Leu Tyr Phe Asn Tyr Met Ala Ser Trp Val
        1300            1305            1310

Met Leu Gly Ile Thr Tyr Arg Asn Asn Ser Leu Met Trp Phe Asp Lys
        1315            1320            1325

Thr Pro Leu Ser Tyr Thr His Trp Arg Ala Gly Arg Pro Thr Ile Lys
    1330            1335            1340

Asn Glu Lys Phe Leu Ala Gly Leu Ser Thr Asp Gly Phe Trp Asp Ile
1345            1350            1355            1360

Gln Thr Phe Lys Val Ile Glu Glu Ala Val Tyr Phe His Gln His Ser
            1365            1370            1375

Ile Leu Ala Cys Lys Ile Glu Met Val Asp Tyr Lys Glu Glu His Asn
            1380            1385            1390
```

-continued

```
Thr Thr Leu Pro Gln Phe Met Pro Tyr Glu Asp Gly Ile Tyr Ser Val
    1395                1400                1405
Ile Gln Lys Lys Val Thr Trp Tyr Glu Ala Leu Asn Met Cys Ser Gln
    1410                1415                1420
Ser Gly Gly His Leu Ala Ser Val His Asn Gln Asn Gly Gln Leu Phe
1425                1430                1435                1440
Leu Glu Asp Ile Val Lys Arg Asp Gly Phe Pro Leu Trp Val Gly Leu
            1445                1450                1455
Ser Ser His Asp Gly Ser Glu Ser Ser Phe Glu Trp Ser Asp Gly Ser
        1460                1465                1470
Thr Phe Asp Tyr Ile Pro Trp Lys Gly Gln Thr Ser Pro Gly Asn Cys
    1475                1480                1485
Val Leu Leu Asp Pro Lys Gly Thr Trp Lys His Glu Lys Cys Asn Ser
    1490                1495                1500
Val Lys Asp Gly Ala Ile Cys Tyr Lys Pro Thr Lys Ser Lys Lys Leu
1505                1510                1515                1520
Ser Arg Leu Thr Tyr Ser Ser Arg Cys Pro Ala Ala Lys Glu Asn Gly
            1525                1530                1535
Ser Arg Trp Ile Gln Tyr Lys Gly His Cys Tyr Lys Ser Asp Gln Ala
        1540                1545                1550
Leu His Ser Phe Ser Glu Ala Lys Lys Leu Cys Ser Lys His Asp His
    1555                1560                1565
Ser Ala Thr Ile Val Ser Ile Lys Asp Glu Asp Glu Asn Lys Phe Val
    1570                1575                1580
Ser Arg Leu Met Arg Glu Asn Asn Ile Thr Met Arg Val Trp Leu
1585                1590                1595                1600
Gly Leu Ser Gln His Ser Val Asp Gln Ser Trp Ser Trp Leu Asp Gly
            1605                1610                1615
Ser Glu Val Thr Phe Val Lys Trp Glu Asn Lys Ser Lys Ser Gly Val
        1620                1625                1630
Gly Arg Cys Ser Met Leu Ile Ala Ser Asn Glu Thr Trp Lys Lys Val
    1635                1640                1645
Glu Cys Glu His Gly Phe Gly Arg Val Val Cys Lys Val Pro Leu Gly
    1650                1655                1660
Pro Asp Tyr Thr Ala Ile Ala Ile Ile Val Ala Thr Leu Ser Ile Leu
1665                1670                1675                1680
Val Leu Met Gly Gly Leu Ile Trp Phe Leu Phe Gln Arg His Arg Leu
            1685                1690                1695
His Leu Ala Gly Phe Ser Ser Val Arg Tyr Ala Gln Gly Val Asn Glu
        1700                1705                1710
Asp Glu Ile Met Leu Pro Ser Phe His Asp
    1715                1720

<210> SEQ ID NO 2
<211> LENGTH: 5169
<212> TYPE: DNA
<213> ORGANISM: Homo sapiens
<220> FEATURE:
<221> NAME/KEY: CDS
<222> LOCATION: (1)..(5166)

<400> SEQUENCE: 2 atg agg aca ggc tgg gcg cac ccc tcg ccg ccc ggc ggg gct cct cat      48
Met Arg Thr Gly Trp Ala His Pro Ser Pro Pro Gly Gly Ala Pro His
  1               5                  10                  15
```

-continued

```
gct gct ctt ctg gtt ctt cga tct cgc gga gcc ctc tgg ccg cgc act         96
Ala Ala Leu Leu Val Leu Arg Ser Arg Gly Ala Leu Trp Pro Arg Thr
         20                  25                  30 aat gac ccc ttc acc atc gtc cat gga aat acg ggc aag tgc atc aag        144
Asn Asp Pro Phe Thr Ile Val His Gly Asn Thr Gly Lys Cys Ile Lys
 35                  40                  45 cca gtg tat ggc tgg ata gta gca gac gac tgt gat gaa act gag gac        192
Pro Val Tyr Gly Trp Ile Val Ala Asp Asp Cys Asp Glu Thr Glu Asp
     50                  55                  60 aag tta tgg aag tgg gtg tcc cag cat cgg ctc ttt cat ttg cac tcc        240
Lys Leu Trp Lys Trp Val Ser Gln His Arg Leu Phe His Leu His Ser
 65                  70                  75                  80 caa aag tgc ctt ggc ctc gat att acc aaa tcg gta aat gag ctg aga        288
Gln Lys Cys Leu Gly Leu Asp Ile Thr Lys Ser Val Asn Glu Leu Arg
                 85                  90                  95 atg ttc agc tgt gac tcc agt gcc atg ctg tgg tgg aaa tgt gag cac        336
Met Phe Ser Cys Asp Ser Ser Ala Met Leu Trp Trp Lys Cys Glu His
             100                 105                 110 cac tct ctg tac gga gct gcc cgg tac tgg ctg gct ctg aag gat gga        384
His Ser Leu Tyr Gly Ala Ala Arg Tyr Trp Leu Ala Leu Lys Asp Gly
         115                 120                 125 cat ggc aca gca atc tca aat gca tct gat gtc tgg aag aaa gga ggc        432
His Gly Thr Ala Ile Ser Asn Ala Ser Asp Val Trp Lys Lys Gly Gly
 130                 135                 140 tca gag gaa agc ctt tgt gac cag cct tat cat gag atc tat acc aga        480
Ser Glu Glu Ser Leu Cys Asp Gln Pro Tyr His Glu Ile Tyr Thr Arg
145                 150                 155                 160 gat ggg aac tct tat ggg aga cct tgt gaa ttt cca ttc tta att gat        528
Asp Gly Asn Ser Tyr Gly Arg Pro Cys Glu Phe Pro Phe Leu Ile Asp
                165                 170                 175 ggg acc tgg cat cat gat tgc att ctt gat gaa gat cat agt ggg cca        576
Gly Thr Trp His His Asp Cys Ile Leu Asp Glu Asp His Ser Gly Pro
            180                 185                 190 tgg tgt gcc acc acc tta aat tat gaa tat gac cga aag tgg ggc atc        624
Trp Cys Ala Thr Thr Leu Asn Tyr Glu Tyr Asp Arg Lys Trp Gly Ile
        195                 200                 205 tgc tta aag cct gaa aac ggt tgt gaa gat aat tgg gaa aag aac gag        672
Cys Leu Lys Pro Glu Asn Gly Cys Glu Asp Asn Trp Glu Lys Asn Glu
    210                 215                 220 cag ttt gga agt tgc tac caa ttt aat act cag acg gct ctt tct tgg        720
Gln Phe Gly Ser Cys Tyr Gln Phe Asn Thr Gln Thr Ala Leu Ser Trp
225                 230                 235                 240 aaa gaa gct tat gtt tca tgt cag aat caa gga gct gat tta ctg agc        768
Lys Glu Ala Tyr Val Ser Cys Gln Asn Gln Gly Ala Asp Leu Leu Ser
                245                 250                 255 atc aac agt gct gct gaa tta act tac ctt aaa gaa aaa gaa ggc att        816
Ile Asn Ser Ala Ala Glu Leu Thr Tyr Leu Lys Glu Lys Glu Gly Ile
            260                 265                 270 gct aag att ttc tgg att ggt tta aat cag cta tac tct gct aga ggc        864
Ala Lys Ile Phe Trp Ile Gly Leu Asn Gln Leu Tyr Ser Ala Arg Gly
        275                 280                 285 tgg gaa tgg tca gac cac aaa cca tta aac ttt ctc aac tgg gat cca        912
Trp Glu Trp Ser Asp His Lys Pro Leu Asn Phe Leu Asn Trp Asp Pro
    290                 295                 300 gac agg ccc agt gca cct act ata ggt ggc tcc agc tgt gca aga atg        960
Asp Arg Pro Ser Ala Pro Thr Ile Gly Gly Ser Ser Cys Ala Arg Met
305                 310                 315                 320 gat gct gag tct ggt ctg tgg cag agc ttt tcc tgt gaa gct caa ctg       1008
Asp Ala Glu Ser Gly Leu Trp Gln Ser Phe Ser Cys Glu Ala Gln Leu
                325                 330                 335
```

```
ccc tat gtc tgc agg aaa cca tta aat aat aca gtg gag tta aca gat      1056
Pro Tyr Val Cys Arg Lys Pro Leu Asn Asn Thr Val Glu Leu Thr Asp
            340                 345                 350 gtc tgg aca tac tca gat acc cgc tgt gat gca ggc tgg ctg cca aat      1104
Val Trp Thr Tyr Ser Asp Thr Arg Cys Asp Ala Gly Trp Leu Pro Asn
        355                 360                 365 aat gga ttt tgc tat ctg ctg gta aat gaa agt aat tcc tgg gat aag      1152
Asn Gly Phe Cys Tyr Leu Leu Val Asn Glu Ser Asn Ser Trp Asp Lys
    370                 375                 380 gca cat gcg aaa tgc aaa gcc ttc agt agt gac cta atc agc att cat      1200
Ala His Ala Lys Cys Lys Ala Phe Ser Ser Asp Leu Ile Ser Ile His
385                 390                 395                 400 tct cta gca gat gtg gag gtg gtt gtc aca aaa ctc cat aat gag gat      1248
Ser Leu Ala Asp Val Glu Val Val Val Thr Lys Leu His Asn Glu Asp
            405                 410                 415 atc aaa gaa gaa gtg tgg ata ggc ctt aag aac ata aac ata cca act      1296
Ile Lys Glu Glu Val Trp Ile Gly Leu Lys Asn Ile Asn Ile Pro Thr
        420                 425                 430 tta ttt cag tgg tca gat ggt act gaa gtt act cta aca tat tgg gat      1344
Leu Phe Gln Trp Ser Asp Gly Thr Glu Val Thr Leu Thr Tyr Trp Asp
    435                 440                 445 gag aat gag cca aat gtt ccc tac aat aag acg ccc aac tgt gtt tcc      1392
Glu Asn Glu Pro Asn Val Pro Tyr Asn Lys Thr Pro Asn Cys Val Ser
450                 455                 460 tac tta gga gag cta ggt cag tgg aaa gtc caa tca tgt gag gag aaa      1440
Tyr Leu Gly Glu Leu Gly Gln Trp Lys Val Gln Ser Cys Glu Glu Lys
            465                 470                 475             480 cta aaa tat gta tgc aag aga aag gga gaa aaa ctg aat gac gca agt      1488
Leu Lys Tyr Val Cys Lys Arg Lys Gly Glu Lys Leu Asn Asp Ala Ser
        485                 490                 495 tct gat aag atg tgt cct cca gat gag ggc tgg aag aga cat gga gaa      1536
Ser Asp Lys Met Cys Pro Pro Asp Glu Gly Trp Lys Arg His Gly Glu
    500                 505                 510 acc tgt tac aag att tat gag gat gag gtc cct ttt gga aca aac tgc      1584
Thr Cys Tyr Lys Ile Tyr Glu Asp Glu Val Pro Phe Gly Thr Asn Cys
515                 520                 525 aat ctg act atc act agc aga ttt gag caa gaa tac cta aat gat ttg      1632
Asn Leu Thr Ile Thr Ser Arg Phe Glu Gln Glu Tyr Leu Asn Asp Leu
            530                 535                 540 atg aaa aag tat gat aaa tct cta aga aaa tac ttc tgg act ggc ctg      1680
Met Lys Lys Tyr Asp Lys Ser Leu Arg Lys Tyr Phe Trp Thr Gly Leu
545                 550                 555                 560 aga gat gta gat tct tgt gga gag tat aac tgg gca act gtt ggt gga      1728
Arg Asp Val Asp Ser Cys Gly Glu Tyr Asn Trp Ala Thr Val Gly Gly
            565                 570                 575 aga agg cgg gct gta acc ttt tcc aac tgg aat ttt ctt gag cca gct      1776
Arg Arg Arg Ala Val Thr Phe Ser Asn Trp Asn Phe Leu Glu Pro Ala
        580                 585                 590 tcc ccg ggc ggc tgc gtg gct atg tct act gga aag tct gtt gga aag      1824
Ser Pro Gly Gly Cys Val Ala Met Ser Thr Gly Lys Ser Val Gly Lys
    595                 600                 605 tgg gag gtg aag gac tgc aga agc ttc aaa gca ctt tca att tgc aag      1872
Trp Glu Val Lys Asp Cys Arg Ser Phe Lys Ala Leu Ser Ile Cys Lys
610                 615                 620 aaa atg agt gga ccc ctt ggg cct gaa gaa gca tcc cct aag cct gat      1920
Lys Met Ser Gly Pro Leu Gly Pro Glu Glu Ala Ser Pro Lys Pro Asp
625                 630                 635                 640 gac ccc tgt cct gaa ggc tgg cag agt ttc ccc gca agt ctt tct tgt      1968
Asp Pro Cys Pro Glu Gly Trp Gln Ser Phe Pro Ala Ser Leu Ser Cys
```

-continued

|  |  |  |
|---|---|---|
| | 645 650 655 | |
| tat aag gta ttc cat gca gaa aga att gta aga aag agg aac tgg gaa<br>Tyr Lys Val Phe His Ala Glu Arg Ile Val Arg Lys Arg Asn Trp Glu<br>660 665 670 | 2016 |
| gaa gct gaa cga ttc tgc caa gcc ctt gga gca cac ctt tct agc ttc<br>Glu Ala Glu Arg Phe Cys Gln Ala Leu Gly Ala His Leu Ser Ser Phe<br>675 680 685 | 2064 |
| agc cat gtg gat gaa ata aag gaa ttt ctt cac ttt tta acg gac cag<br>Ser His Val Asp Glu Ile Lys Glu Phe Leu His Phe Leu Thr Asp Gln<br>690 695 700 | 2112 |
| ttc agt ggc cag cat tgg ctg tgg att ggt ttg aat aaa agg agc cca<br>Phe Ser Gly Gln His Trp Leu Trp Ile Gly Leu Asn Lys Arg Ser Pro<br>705 710 715 720 | 2160 |
| gat tta caa gga tcc tgg caa tgg agt gat cgt aca cca gtg tct act<br>Asp Leu Gln Gly Ser Trp Gln Trp Ser Asp Arg Thr Pro Val Ser Thr<br>725 730 735 | 2208 |
| att atc atg cca aat gag ttt cag cag gat tat gac atc aga gac tgt<br>Ile Ile Met Pro Asn Glu Phe Gln Gln Asp Tyr Asp Ile Arg Asp Cys<br>740 745 750 | 2256 |
| gct gct gtc aag gta ttt cat agg cca tgg cga aga ggc tgg cat ttc<br>Ala Ala Val Lys Val Phe His Arg Pro Trp Arg Arg Gly Trp His Phe<br>755 760 765 | 2304 |
| tat gat gat aga gaa ttt att tat ttg agg cct ttt gct tgt gat aca<br>Tyr Asp Asp Arg Glu Phe Ile Tyr Leu Arg Pro Phe Ala Cys Asp Thr<br>770 775 780 | 2352 |
| aaa ctt gaa tgg gtg tgc caa att cca aaa ggc cgt act cca aaa aca<br>Lys Leu Glu Trp Val Cys Gln Ile Pro Lys Gly Arg Thr Pro Lys Thr<br>785 790 795 800 | 2400 |
| cca gac tgg tac aat cca gac cgt gct gga att cat gga cct cca ctt<br>Pro Asp Trp Tyr Asn Pro Asp Arg Ala Gly Ile His Gly Pro Pro Leu<br>805 810 815 | 2448 |
| ata att gaa gga agt gaa tat tgg ttt gtt gct gat ctt cac cta aac<br>Ile Ile Glu Gly Ser Glu Tyr Trp Phe Val Ala Asp Leu His Leu Asn<br>820 825 830 | 2496 |
| tat gaa gaa gcc gtc ctg tac tgt gcc agc aat cac agc ttt ctt gcg<br>Tyr Glu Glu Ala Val Leu Tyr Cys Ala Ser Asn His Ser Phe Leu Ala<br>835 840 845 | 2544 |
| act ata aca tct ttt gtg gga cta aaa gcc atc aaa aac aaa ata gca<br>Thr Ile Thr Ser Phe Val Gly Leu Lys Ala Ile Lys Asn Lys Ile Ala<br>850 855 860 | 2592 |
| aat ata tct ggt gat gga cag aag tgg tgg ata aga att agc gag tgg<br>Asn Ile Ser Gly Asp Gly Gln Lys Trp Trp Ile Arg Ile Ser Glu Trp<br>865 870 875 880 | 2640 |
| cca ata gat gat cat ttt aca tac tca cga tat cca tgg cac cgc ttt<br>Pro Ile Asp Asp His Phe Thr Tyr Ser Arg Tyr Pro Trp His Arg Phe<br>885 890 895 | 2688 |
| cct gtg aca ttt gga gag gaa tgc ttg tac atg tct gcc aag act tgg<br>Pro Val Thr Phe Gly Glu Glu Cys Leu Tyr Met Ser Ala Lys Thr Trp<br>900 905 910 | 2736 |
| ctt atc gac tta ggt aaa cca aca gac tgt agt acc aag ttg ccc ttc<br>Leu Ile Asp Leu Gly Lys Pro Thr Asp Cys Ser Thr Lys Leu Pro Phe<br>915 920 925 | 2784 |
| atc tgt gaa aaa tat aat gtt tct tcg tta gag aaa tac agc cca gat<br>Ile Cys Glu Lys Tyr Asn Val Ser Ser Leu Glu Lys Tyr Ser Pro Asp<br>930 935 940 | 2832 |
| tct gca gct aaa gtg caa tgt tct gag caa tgg att cct ttt cag aat<br>Ser Ala Ala Lys Val Gln Cys Ser Glu Gln Trp Ile Pro Phe Gln Asn<br>945 950 955 960 | 2880 |
| aag tgt ttt cta aag atc aaa ccc gtg tct ctc aca ttt tct caa gca | 2928 |

```
Lys Cys Phe Leu Lys Ile Lys Pro Val Ser Leu Thr Phe Ser Gln Ala
            965                 970                 975 agc gat acc tgt cac tcc tat ggt ggc acc ctt cct tca gtg ttg agc      2976
Ser Asp Thr Cys His Ser Tyr Gly Gly Thr Leu Pro Ser Val Leu Ser
        980                 985                 990 cag att gaa caa gac ttt att aca tcc ttg ctt ccg gat atg gaa gct      3024
Gln Ile Glu Gln Asp Phe Ile Thr Ser Leu Leu Pro Asp Met Glu Ala
    995                 1000                1005 act tta tgg att ggt ttg cgc tgg act gcc tat gaa aag ata aac aaa      3072
Thr Leu Trp Ile Gly Leu Arg Trp Thr Ala Tyr Glu Lys Ile Asn Lys
1010                1015                1020 tgg aca gat aac aga gag ctg acg tac agt aac ttt cac cca tta ttg      3120
Trp Thr Asp Asn Arg Glu Leu Thr Tyr Ser Asn Phe His Pro Leu Leu
1025                1030                1035                1040 gtt agt ggg agg ctg aga ata cca gaa aat ttt ttt gag gaa gag tct      3168
Val Ser Gly Arg Leu Arg Ile Pro Glu Asn Phe Phe Glu Glu Glu Ser
                1045                1050                1055 cgc tac cac tgt gcc cta ata ctc aac ctc caa aaa tca ccg ttt act      3216
Arg Tyr His Cys Ala Leu Ile Leu Asn Leu Gln Lys Ser Pro Phe Thr
            1060                1065                1070 ggg acg tgg aat ttt aca tcc tgc agt gaa cgc cac ttt gtg tct ctc      3264
Gly Thr Trp Asn Phe Thr Ser Cys Ser Glu Arg His Phe Val Ser Leu
        1075                1080                1085 tgt cag aaa tat tca gaa gtt aaa agc aga cag acg ttg cag aat gct      3312
Cys Gln Lys Tyr Ser Glu Val Lys Ser Arg Gln Thr Leu Gln Asn Ala
    1090                1095                1100 tca gaa act gta aag tat cta aat aat ctg tac aaa ata atc cca aag      3360
Ser Glu Thr Val Lys Tyr Leu Asn Asn Leu Tyr Lys Ile Ile Pro Lys
1105                1110                1115                1120 act ctg act tgg cac agt gct aaa agg gag tgt ctg aaa agt aac atg      3408
Thr Leu Thr Trp His Ser Ala Lys Arg Glu Cys Leu Lys Ser Asn Met
                1125                1130                1135 cag ctg gtg agc atc acg gac cct tac cag cag gca ttc ctc agt gtg      3456
Gln Leu Val Ser Ile Thr Asp Pro Tyr Gln Gln Ala Phe Leu Ser Val
            1140                1145                1150 cag gcg ctc ctt cac aac tct tcc tta tgg atc gga ctc ttc agt caa      3504
Gln Ala Leu Leu His Asn Ser Ser Leu Trp Ile Gly Leu Phe Ser Gln
        1155                1160                1165 gat gat gaa ctc aac ttt ggt tgg tca gat ggg aaa cgt ctt cat ttt      3552
Asp Asp Glu Leu Asn Phe Gly Trp Ser Asp Gly Lys Arg Leu His Phe
    1170                1175                1180 agt cgc tgg gct gaa act aat ggg caa ctc gaa gac tgt gta gta tta      3600
Ser Arg Trp Ala Glu Thr Asn Gly Gln Leu Glu Asp Cys Val Val Leu
1185                1190                1195                1200 gac act gat gga ttc tgg aaa aca gtt gat tgc aat gac aat caa cca      3648
Asp Thr Asp Gly Phe Trp Lys Thr Val Asp Cys Asn Asp Asn Gln Pro
                1205                1210                1215 ggt gct att tgc tac tat tca gga aat gag act gaa aaa gag gtc aaa      3696
Gly Ala Ile Cys Tyr Tyr Ser Gly Asn Glu Thr Glu Lys Glu Val Lys
            1220                1225                1230 cca gtt gac agt gtt aaa tgt cca tct cct gtt cta aat act ccg tgg      3744
Pro Val Asp Ser Val Lys Cys Pro Ser Pro Val Leu Asn Thr Pro Trp
        1235                1240                1245 ata cca ttt cag aac tgt tgc tac aat ttc ata ata aca aag aat agg      3792
Ile Pro Phe Gln Asn Cys Cys Tyr Asn Phe Ile Ile Thr Lys Asn Arg
    1250                1255                1260 cat atg gca aca aca cag gat gaa gtt cat act aaa tgc cag aaa ctg      3840
His Met Ala Thr Thr Gln Asp Glu Val His Thr Lys Cys Gln Lys Leu
1265                1270                1275                1280
```

-continued

| | |
|---|---|
| aat cca aaa tca cat att ctg agt att cga gat gaa aag gag aat aac<br>Asn Pro Lys Ser His Ile Leu Ser Ile Arg Asp Glu Lys Glu Asn Asn<br>                1285                    1290                    1295 | 3888 |
| ttt gtt ctt gag caa ctg ctg tac ttc aat tat atg gct tca tgg gtc<br>Phe Val Leu Glu Gln Leu Leu Tyr Phe Asn Tyr Met Ala Ser Trp Val<br>1300                    1305                    1310 | 3936 |
| atg tta gga ata act tat aga aat aat tct ctt atg tgg ttt gat aag<br>Met Leu Gly Ile Thr Tyr Arg Asn Asn Ser Leu Met Trp Phe Asp Lys<br>                1315                    1320                    1325 | 3984 |
| acc cca ctg tca tat aca cat tgg aga gca gga aga cca act ata aaa<br>Thr Pro Leu Ser Tyr Thr His Trp Arg Ala Gly Arg Pro Thr Ile Lys<br>1330                    1335                    1340 | 4032 |
| aat gag aag ttt ttg gct ggt tta agt act gac ggc ttc tgg gat att<br>Asn Glu Lys Phe Leu Ala Gly Leu Ser Thr Asp Gly Phe Trp Asp Ile<br>1345                    1350                    1355                    1360 | 4080 |
| caa acc ttt aaa gtt att gaa gaa gca gtt tat ttt cac cag cac agc<br>Gln Thr Phe Lys Val Ile Glu Glu Ala Val Tyr Phe His Gln His Ser<br>                1365                    1370                    1375 | 4128 |
| att ctt gct tgt aaa att gaa atg gtt gac tac aaa gaa gaa cat aat<br>Ile Leu Ala Cys Lys Ile Glu Met Val Asp Tyr Lys Glu Glu His Asn<br>1380                    1385                    1390 | 4176 |
| act aca ctg cca cag ttt atg cca tat gaa gat ggt att tac agt gtt<br>Thr Thr Leu Pro Gln Phe Met Pro Tyr Glu Asp Gly Ile Tyr Ser Val<br>                1395                    1400                    1405 | 4224 |
| att caa aaa aag gta aca tgg tat gaa gca tta aac atg tgt tct caa<br>Ile Gln Lys Lys Val Thr Trp Tyr Glu Ala Leu Asn Met Cys Ser Gln<br>1410                    1415                    1420 | 4272 |
| agt gga ggt cac ttg gca agc gtt cac aac caa aat ggc cag ctc ttt<br>Ser Gly Gly His Leu Ala Ser Val His Asn Gln Asn Gly Gln Leu Phe<br>1425                    1430                    1435                    1440 | 4320 |
| ctg gaa gat att gta aaa cgt gat gga ttt cca cta tgg gtt ggg ctc<br>Leu Glu Asp Ile Val Lys Arg Asp Gly Phe Pro Leu Trp Val Gly Leu<br>                1445                    1450                    1455 | 4368 |
| tca agt cat gat gga agt gaa tca agt ttt gaa tgg tct gat ggt agt<br>Ser Ser His Asp Gly Ser Glu Ser Ser Phe Glu Trp Ser Asp Gly Ser<br>1460                    1465                    1470 | 4416 |
| aca ttt gac tat atc cca tgg aaa ggc caa aca tct cct gga aat tgt<br>Thr Phe Asp Tyr Ile Pro Trp Lys Gly Gln Thr Ser Pro Gly Asn Cys<br>                1475                    1480                    1485 | 4464 |
| gtt ctc ttg gat cca aaa gga act tgg aaa cat gaa aaa tgc aac tct<br>Val Leu Leu Asp Pro Lys Gly Thr Trp Lys His Glu Lys Cys Asn Ser<br>1490                    1495                    1500 | 4512 |
| gtt aag gat ggt gct att tgt tat aaa cct aca aaa tct aaa aag ctg<br>Val Lys Asp Gly Ala Ile Cys Tyr Lys Pro Thr Lys Ser Lys Lys Leu<br>1505                    1510                    1515                    1520 | 4560 |
| tcc cgt ctt aca tat tca tca aga tgt cca gca gca aaa gag aat ggg<br>Ser Arg Leu Thr Tyr Ser Ser Arg Cys Pro Ala Ala Lys Glu Asn Gly<br>                1525                    1530                    1535 | 4608 |
| tca cgg tgg atc cag tac aag ggt cac tgt tac aag tct gat cag gca<br>Ser Arg Trp Ile Gln Tyr Lys Gly His Cys Tyr Lys Ser Asp Gln Ala<br>1540                    1545                    1550 | 4656 |
| ttg cac agt ttt tca gag gcc aaa aaa ttg tgt tca aaa cat gat cac<br>Leu His Ser Phe Ser Glu Ala Lys Lys Leu Cys Ser Lys His Asp His<br>                1555                    1560                    1565 | 4704 |
| tct gca act atc gtt tcc ata aaa gat gaa gat gag aat aaa ttt gtg<br>Ser Ala Thr Ile Val Ser Ile Lys Asp Glu Asp Glu Asn Lys Phe Val<br>1570                    1575                    1580 | 4752 |
| agc aga ctg atg agg gaa aat aat aac att acc atg aga gtt tgg ctt<br>Ser Arg Leu Met Arg Glu Asn Asn Asn Ile Thr Met Arg Val Trp Leu<br>1585                    1590                    1595                    1600 | 4800 |

|   |   |   |   |   |   |   |   |   |   |   |   |   |   |   |   |      |
|---|---|---|---|---|---|---|---|---|---|---|---|---|---|---|---|------|
| gga | tta | tct | caa | cat | tct | gtt | gac | cag | tct | tgg | agt | tgg | tta | gat | gga | 4848 |
| Gly | Leu | Ser | Gln | His | Ser | Val | Asp | Gln | Ser | Trp | Ser | Trp | Leu | Asp | Gly |      |
|     |     |     |     | 1605 |     |     |     | 1610 |     |     |     | 1615 |     |     |     |      |

|   |   |   |   |   |   |   |   |   |   |   |   |   |   |   |   |      |
|---|---|---|---|---|---|---|---|---|---|---|---|---|---|---|---|------|
| tca | gaa | gtg | aca | ttt | gtc | aaa | tgg | gaa | aat | aaa | agt | aag | agt | ggt | gtt | 4896 |
| Ser | Glu | Val | Thr | Phe | Val | Lys | Trp | Glu | Asn | Lys | Ser | Lys | Ser | Gly | Val |      |
|     |     |     | 1620 |     |     |     | 1625 |     |     |     | 1630 |     |     |     |     |      |

|   |   |   |   |   |   |   |   |   |   |   |   |   |   |   |   |      |
|---|---|---|---|---|---|---|---|---|---|---|---|---|---|---|---|------|
| gga | aga | tgt | agc | atg | ttg | ata | gct | tca | aat | gaa | act | tgg | aaa | aaa | gtt | 4944 |
| Gly | Arg | Cys | Ser | Met | Leu | Ile | Ala | Ser | Asn | Glu | Thr | Trp | Lys | Lys | Val |      |
|     | 1635 |     |     |     | 1640 |     |     |     | 1645 |     |     |     |     |     |     |      |

|   |   |   |   |   |   |   |   |   |   |   |   |   |   |   |   |      |
|---|---|---|---|---|---|---|---|---|---|---|---|---|---|---|---|------|
| gaa | tgt | gaa | cat | ggt | ttt | gga | aga | gtt | gtc | tgc | aaa | gtg | cct | ctg | ggc | 4992 |
| Glu | Cys | Glu | His | Gly | Phe | Gly | Arg | Val | Val | Cys | Lys | Val | Pro | Leu | Gly |      |
|     | 1650 |     |     |     | 1655 |     |     |     | 1660 |     |     |     |     |     |     |      |

|   |   |   |   |   |   |   |   |   |   |   |   |   |   |   |   |      |
|---|---|---|---|---|---|---|---|---|---|---|---|---|---|---|---|------|
| cct | gat | tac | aca | gca | ata | gct | atc | ata | gtt | gcc | aca | cta | agt | atc | tta | 5040 |
| Pro | Asp | Tyr | Thr | Ala | Ile | Ala | Ile | Ile | Val | Ala | Thr | Leu | Ser | Ile | Leu |      |
| 1665 |     |     |     | 1670 |     |     |     | 1675 |     |     |     | 1680 |     |     |     |      |

|   |   |   |   |   |   |   |   |   |   |   |   |   |   |   |   |      |
|---|---|---|---|---|---|---|---|---|---|---|---|---|---|---|---|------|
| gtt | ctc | atg | ggc | gga | ctg | att | tgg | ttc | ctc | ttc | caa | agg | cac | cgt | ttg | 5088 |
| Val | Leu | Met | Gly | Gly | Leu | Ile | Trp | Phe | Leu | Phe | Gln | Arg | His | Arg | Leu |      |
|     |     |     | 1685 |     |     |     | 1690 |     |     |     | 1695 |     |     |     |     |      |

|   |   |   |   |   |   |   |   |   |   |   |   |   |   |   |   |      |
|---|---|---|---|---|---|---|---|---|---|---|---|---|---|---|---|------|
| cac | ctg | gcg | ggt | ttc | tca | tca | gtt | cga | tat | gca | caa | gga | gtg | aat | gaa | 5136 |
| His | Leu | Ala | Gly | Phe | Ser | Ser | Val | Arg | Tyr | Ala | Gln | Gly | Val | Asn | Glu |      |
|     |     |     | 1700 |     |     |     | 1705 |     |     |     | 1710 |     |     |     |     |      |

|   |   |   |   |   |   |   |   |   |      |
|---|---|---|---|---|---|---|---|---|------|
| gat | gag | att | atg | ctt | cct | tct | ttc | cat | gac | taa | 5169 |
| Asp | Glu | Ile | Met | Leu | Pro | Ser | Phe | His | Asp |     |      |
|     | 1715 |     |     |     | 1720 |     |     |     |     |     |      |

<210> SEQ ID NO 3
<211> LENGTH: 349
<212> TYPE: DNA
<213> ORGANISM: Homo sapiens

<400> SEQUENCE: 3

| aacagttgat tgcaatgaca atcaaccagg tgctatttgc tactattcag gaaatgagac | 60 |
| tgaaaaagag gtcaaaccag ttgacagtgt taaatgtcca tctcctgttc taaatactcc | 120 |
| gtggatacca tttcagaact gttgctacaa tttcataata acaaagaata ggcatatggc | 180 |
| aacaacacag gatgaagttc atactaaatg ccagaaactg aatccaaaat cacatattct | 240 |
| gagtattcga gatgaaaagg agaataactt tgttcttgag caactgctgt acttcaatta | 300 |
| tatggcttca tgggtcatgt taggaataac ttatagaaat aaktctctt | 349 |

<210> SEQ ID NO 4
<211> LENGTH: 152
<212> TYPE: DNA
<213> ORGANISM: Homo sapiens

<400> SEQUENCE: 4

| attaatatgc tgtggaagtg ggtgtcccag catcggctct ttcatttgca ctcccaaaag | 60 |
| tgccttggcc tcgatattac caaatcggta aatgagctga gaatgttcag ctgtgactcc | 120 |
| gtgccatgc tgtggtggaa atgcgagcac ca | 152 |

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (6)
<223> OTHER INFORMATION: a, t, c or g
<221> NAME/KEY: modified_base
<222> LOCATION: (12)

```
<223> OTHER INFORMATION: a, t, c or g

<400> SEQUENCE: 5
gaycangayg gnttytggaa                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (18)
<223> OTHER INFORMATION: a, t, c or g

<400> SEQUENCE: 6
tacaccaarc trttytgncg                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (9)
<223> OTHER INFORMATION: a, t, c or g

<400> SEQUENCE: 7
aayatgctnt ggaartgggt                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
tgrtgytcrc ayttccacca                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (6)
<223> OTHER INFORMATION: a, t, c or g
<221> NAME/KEY: modified_base
<222> LOCATION: (12)
<223> OTHER INFORMATION: a, t, c or g

<400> SEQUENCE: 9
gayacngayg gnttytggaa                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (3)
<223> OTHER INFORMATION: a, t, c or g

<400> SEQUENCE: 10
```

-continued gcngtyttrt craaccacat                                                            20

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 11
gctctagaaa catgacccat gaagcc                                                     26

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 12
gctctagaca tcggctcttt catttgt                                                    27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 13
cgggattcac agttgattgc aatgaca                                                    27

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Oligo d(T)
      adaptor primer

<400> SEQUENCE: 14
gactagtctg cagaattctt tttttttttt ttttt                                           35

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Adaptor
      primer

<400> SEQUENCE: 15
gactagtctg cagaattc                                                              18

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 16
cgggatccct ctggccgcgc actaatga                                                   28

<210> SEQ ID NO 17
<211> LENGTH: 31

```
<212> TYPE: DNA
<213> ORGANISM: Artificial Sequence
<220> FEATURE:
<223> OTHER INFORMATION: Description of Artificial Sequence: Primer

<400> SEQUENCE: 17
ccgctcgagc tgtggatacc agcacatgcc t                                    31

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 18
gatgggaact cttatgggag acct                                            24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 19
tgatgcaggc tggctgccaa ataa                                            24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 20
aactgggcaa ctgttggtgg aaga                                            24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 21
atggcgaaga ggctggcatt tcta                                            24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 22
ctcaagcaag cgatacctgt cact                                            24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 23
```
tgggcaactc gaagactgtg tagt                                              24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 24
caccagcaca gcattcttgc ttgt                                              24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 25
atttgtgagc agactgatga ggga                                              24

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence:
      PCR-fragment

<400> SEQUENCE: 26
cggaattcga tctcatgata aggctggtca ca                                     32

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Primer 060

<400> SEQUENCE: 27
gtggatccag tacaagggtc a                                                 21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Primer 056

<400> SEQUENCE: 28
accaaatcag tccgcccatg a                                                 21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Primer 053

<400> SEQUENCE: 29
atggggaagg tgaaggtcgg a                                                 21

<210> SEQ ID NO 30
<211> LENGTH: 21
<212> TYPE: DNA

-continued

```
<213> ORGANISM: Artificial Sequence
<220> FEATURE:
<223> OTHER INFORMATION: Description of Artificial Sequence: Primer 053

<400> SEQUENCE: 30
aggggccatc cacagtcttc t                                          21

<210> SEQ ID NO 31
<211> LENGTH: 1723
<212> TYPE: PRT
<213> ORGANISM: Murine sp.

<400> SEQUENCE: 31
```

Met Arg Thr Gly Arg Val Thr Pro Gly Leu Ala Ala Gly Leu Leu Leu
 1               5                  10                  15

Leu Leu Leu Arg Ser Phe Gly Leu Val Glu Pro Ser Glu Ser Ser Gly
            20                  25                  30

Asn Asp Pro Phe Thr Ile Val His Glu Asn Thr Gly Lys Cys Ile Gln
        35                  40                  45

Pro Leu Ser Asp Trp Val Val Ala Gln Asp Cys Ser Gly Thr Asn Asn
    50                  55                  60

Met Leu Trp Lys Trp Val Ser Gln His Arg Leu Phe His Leu Glu Ser
65                  70                  75                  80

Gln Lys Cys Leu Gly Leu Asp Ile Thr Lys Ala Thr Asp Asn Leu Arg
                85                  90                  95

Met Phe Ser Cys Asp Ser Thr Val Met Leu Trp Trp Lys Cys Glu His
            100                 105                 110

His Ser Leu Tyr Thr Ala Ala Gln Tyr Arg Leu Ala Leu Lys Asp Gly
        115                 120                 125

Tyr Ala Val Ala Asn Thr Asn Thr Ser Asp Val Trp Lys Lys Gly Gly
    130                 135                 140

Ser Glu Glu Asn Leu Cys Ala Gln Pro Tyr His Glu Ile Tyr Thr Arg
145                 150                 155                 160

Asp Gly Asn Ser Tyr Gly Arg Pro Cys Glu Phe Pro Phe Leu Ile Gly
                165                 170                 175

Glu Thr Trp Tyr His Asp Cys Ile His Asp Glu Asp His Ser Gly Pro
            180                 185                 190

Trp Cys Ala Thr Thr Leu Ser Tyr Glu Tyr Asp Gln Lys Trp Gly Ile
        195                 200                 205

Cys Leu Leu Pro Glu Ser Gly Cys Glu Gly Asn Trp Glu Lys Asn Glu
    210                 215                 220

Gln Ile Gly Ser Cys Tyr Gln Phe Asn Asn Gln Glu Ile Leu Ser Trp
225                 230                 235                 240

Lys Glu Ala Tyr Val Ser Cys Gln Asn Gln Gly Ala Asp Leu Leu Ser
                245                 250                 255

Ile His Ser Ala Ala Glu Leu Ala Tyr Ile Thr Gly Lys Glu Asp Ile
            260                 265                 270

Ala Arg Leu Val Trp Leu Gly Leu Asn Gln Leu Tyr Ser Ala Arg Gly
        275                 280                 285

Trp Glu Trp Ser Asp Phe Arg Pro Leu Lys Phe Leu Asn Trp Asp Pro
    290                 295                 300

Gly Thr Pro Val Ala Pro Val Ile Gly Gly Ser Ser Cys Ala Arg Met
305                 310                 315                 320

Asp Thr Glu Ser Gly Leu Trp Gln Ser Val Ser Cys Glu Ser Gln Gln
                325                 330                 335

-continued

```
Pro Tyr Val Cys Lys Lys Pro Leu Asn Asn Thr Leu Glu Leu Pro Asp
            340                 345                 350

Val Trp Thr Tyr Thr Asp Thr His Cys His Val Gly Trp Leu Pro Asn
            355                 360                 365

Asn Gly Phe Cys Tyr Leu Leu Ala Asn Glu Ser Ser Ser Trp Asp Ala
            370                 375                 380

Ala His Leu Lys Cys Lys Ala Phe Gly Ala Asp Leu Ile Ser Met His
385                 390                 395                 400

Ser Leu Ala Asp Val Glu Val Val Thr Lys Leu His Asn Gly Asp
                405                 410                 415

Val Lys Lys Glu Ile Trp Thr Gly Leu Lys Asn Thr Asn Ser Pro Ala
            420                 425                 430

Leu Phe Gln Trp Ser Asp Gly Thr Glu Val Thr Leu Thr Tyr Trp Asn
            435                 440                 445

Glu Asn Glu Pro Ser Val Pro Phe Asn Lys Thr Pro Asn Cys Val Ser
        450                 455                 460

Tyr Leu Gly Lys Leu Gly Gln Trp Lys Val Gln Ser Cys Glu Lys Lys
465                 470                 475                 480

Leu Arg Tyr Val Cys Lys Lys Gly Glu Ile Thr Lys Asp Ala Glu
                485                 490                 495

Ser Asp Lys Leu Cys Pro Pro Asp Glu Gly Trp Lys Arg His Gly Glu
            500                 505                 510

Thr Cys Tyr Lys Ile Tyr Glu Lys Glu Ala Pro Phe Gly Thr Asn Cys
            515                 520                 525

Asn Leu Thr Ile Thr Ser Arg Phe Glu Gln Glu Phe Leu Asn Tyr Met
        530                 535                 540

Met Lys Asn Tyr Asp Lys Ser Leu Arg Lys Tyr Phe Trp Thr Gly Leu
545                 550                 555                 560

Arg Asp Pro Asp Ser Arg Gly Glu Tyr Ser Trp Ala Val Ala Gln Gly
                565                 570                 575

Val Lys Gln Ala Val Thr Phe Ser Asn Trp Asn Phe Leu Glu Pro Ala
            580                 585                 590

Ser Pro Gly Gly Cys Val Ala Met Ser Thr Gly Lys Thr Leu Gly Lys
            595                 600                 605

Trp Glu Val Lys Asn Cys Arg Ser Phe Arg Ala Leu Ser Ile Cys Lys
            610                 615                 620

Lys Val Ser Glu Pro Gln Glu Pro Glu Glu Ala Ala Pro Lys Pro Asp
625                 630                 635                 640

Asp Pro Cys Pro Glu Gly Trp His Thr Phe Pro Ser Ser Leu Ser Cys
            645                 650                 655

Tyr Lys Val Phe His Ile Glu Arg Ile Val Arg Lys Arg Asn Trp Glu
            660                 665                 670

Glu Ala Glu Arg Phe Cys Gln Ala Leu Gly Ala His Leu Pro Ser Phe
        675                 680                 685

Ser Arg Arg Glu Glu Ile Lys Asp Phe Val His Leu Leu Lys Asp Gln
        690                 695                 700

Phe Ser Gly Gln Arg Trp Leu Trp Ile Gly Leu Asn Lys Arg Ser Pro
705                 710                 715                 720

Asp Leu Gln Gly Ser Trp Gln Trp Ser Asp Arg Thr Pro Val Ser Ala
                725                 730                 735

Val Met Met Glu Pro Glu Phe Gln Gln Asp Phe Asp Ile Arg Asp Cys
            740                 745                 750

Ala Ala Ile Lys Val Leu Asp Val Pro Trp Arg Arg Val Trp His Leu
```

-continued

```
                755                 760                 765

Tyr Glu Asp Lys Asp Tyr Ala Tyr Trp Lys Pro Phe Ala Cys Asp Ala
        770                 775                 780

Lys Leu Glu Trp Val Cys Gln Ile Pro Lys Gly Ser Thr Pro Gln Met
    785                 790                 795                 800

Pro Asp Trp Tyr Asn Pro Glu Arg Thr Gly Ile His Gly Pro Val
                    805                 810                 815

Ile Ile Glu Gly Ser Glu Tyr Trp Phe Val Ala Asp Pro His Leu Asn
                    820                 825                 830

Tyr Glu Ala Val Leu Tyr Cys Ala Ser Asn His Ser Phe Leu Ala
                835                 840                 845

Thr Ile Thr Ser Phe Thr Gly Leu Lys Ala Ile Lys Asn Lys Leu Ala
        850                 855                 860

Asn Ile Ser Gly Glu Glu Gln Lys Trp Trp Val Lys Thr Ser Glu Asn
    865                 870                 875                 880

Pro Ile Asp Arg Tyr Phe Leu Gly Ser Arg Arg Leu Trp His His
                    885                 890                 895

Phe Pro Met Thr Phe Gly Asp Glu Cys Leu His Met Ser Ala Lys Thr
                900                 905                 910

Trp Leu Val Asp Leu Ser Lys Arg Ala Asp Cys Asn Ala Lys Leu Pro
        915                 920                 925

Phe Ile Cys Glu Arg Tyr Asn Val Ser Ser Leu Glu Lys Tyr Ser Pro
        930                 935                 940

Asp Pro Ala Ala Lys Val Gln Cys Thr Glu Lys Trp Ile Pro Phe Gln
    945                 950                 955                 960

Asn Lys Cys Phe Leu Lys Val Asn Ser Gly Pro Val Thr Phe Ser Gln
                    965                 970                 975

Ala Ser Gly Ile Cys His Ser Tyr Gly Gly Thr Leu Pro Ser Val Leu
                980                 985                 990

Ser Arg Gly Glu Gln Asp Phe Ile Ile Ser Leu Leu Pro Glu Met Glu
                995                 1000                1005

Ala Ser Leu Trp Ile Gly Leu Arg Trp Thr Ala Tyr Glu Arg Ile Asn
        1010                1015                1020

Arg Trp Thr Asp Asn Arg Glu Leu Thr Tyr Ser Asn Phe His Pro Leu
    1025                1030                1035                1040

Leu Val Gly Arg Arg Leu Ser Ile Pro Thr Asn Phe Phe Asp Glu
                    1045                1050                1055

Ser His Phe His Cys Ala Leu Ile Leu Asn Leu Lys Lys Ser Pro Leu
                    1060                1065                1070

Thr Gly Thr Trp Asn Phe Thr Ser Cys Ser Glu Arg His Ser Leu Ser
                1075                1080                1085

Leu Cys Gln Lys Tyr Ser Glu Thr Glu Asp Gly Gln Pro Trp Glu Asn
        1090                1095                1100

Thr Ser Lys Thr Val Lys Tyr Leu Asn Asn Leu Tyr Lys Ile Ile Ser
    1105                1110                1115                1120

Lys Pro Leu Thr Trp His Gly Ala Leu Lys Glu Cys Met Lys Glu Lys
                    1125                1130                1135

Met Arg Leu Val Ser Ile Thr Asp Pro Tyr Gln Gln Ala Phe Leu Ala
                1140                1145                1150

Val Gln Ala Thr Leu Arg Asn Ser Ser Phe Trp Ile Gly Leu Ser Ser
                1155                1160                1165

Gln Asp Asp Glu Leu Asn Phe Gly Trp Ser Asp Gly Lys Arg Leu Gln
        1170                1175                1180
```

-continued

```
Phe Ser Asn Trp Ala Gly Ser Asn Glu Gln Leu Asp Asp Cys Val Ile
1185                1190                1195                1200

Leu Asp Thr Asp Gly Phe Trp Lys Thr Ala Asp Cys Asp Asp Asn Gln
            1205                1210                1215

Pro Gly Ala Ile Cys Tyr Tyr Pro Gly Asn Glu Thr Glu Glu Glu Val
        1220                1225                1230

Arg Ala Leu Asp Thr Ala Lys Cys Pro Ser Pro Val Gln Ser Thr Pro
    1235                1240                1245

Trp Ile Pro Phe Gln Asn Ser Cys Tyr Phe Asn Met Ile Thr Asn Asn
1250                1255                1260

Arg His Lys Thr Val Thr Pro Glu Glu Val Gln Ser Thr Cys Glu Lys
1265                1270                1275                1280

Leu His Pro Lys Ala His Ser Leu Ser Ile Arg Asn Glu Glu Glu Asn
            1285                1290                1295

Thr Phe Val Val Glu Gln Leu Leu Tyr Phe Asn Tyr Ile Ala Ser Trp
        1300                1305                1310

Val Met Leu Gly Ile Thr Tyr Glu Asn Asn Ser Leu Met Trp Phe Asp
    1315                1320                1325

Lys Thr Ala Leu Ser Tyr Thr His Trp Arg Thr Gly Arg Pro Thr Val
1330                1335                1340

Lys Asn Gly Lys Phe Leu Ala Gly Leu Ser Thr Asp Gly Phe Trp Asp
1345                1350                1355                1360

Ile Gln Ser Phe Asn Val Ile Glu Glu Thr Leu His Phe Tyr Gln His
            1365                1370                1375

Ser Ile Ser Ala Cys Lys Ile Lys Met Val Asp Tyr Glu Asp Lys His
        1380                1385                1390

Asn Gly Thr Leu Pro Gln Phe Ile Pro Tyr Lys Asp Gly Val Tyr Ser
    1395                1400                1405

Val Ile Gln Lys Lys Val Thr Trp Tyr Glu Ala Leu Asn Ala Cys Ser
1410                1415                1420

Gln Ser Gly Gly Glu Leu Ala Ser Val His Asn Pro Asn Gly Lys Leu
1425                1430                1435                1440

Phe Leu Glu Asp Ile Val Asn Arg Asp Gly Phe Pro Leu Asn Val Gly
            1445                1450                1455

Leu Ser Ser His Asp Gly Ser Glu Ser Ser Phe Glu Trp Ser Asp Gly
        1460                1465                1470

Arg Ala Phe Asp Tyr Val Pro Trp Gln Ser Leu Gln Ser Pro Gly Asp
    1475                1480                1485

Cys Val Val Leu Tyr Pro Lys Gly Ile Trp Arg Arg Glu Lys Cys Leu
1490                1495                1500

Ser Val Lys Asp Gly Ala Ile Cys Tyr Lys Pro Thr Lys Asp Lys Lys
1505                1510                1515                1520

Leu Ile Phe His Val Lys Ser Ser Lys Cys Pro Val Ala Lys Arg Asp
            1525                1530                1535

Gly Pro Gln Trp Val Gln Tyr Gly Gly His Cys Tyr Ala Ser Asp Gln
        1540                1545                1550

Val Leu His Ser Phe Ser Glu Ala Lys Gln Val Cys Gln Glu Leu Asp
    1555                1560                1565

His Ser Ala Thr Val Val Thr Ile Ala Asp Glu Asn Glu Asn Lys Phe
1570                1575                1580

Val Ser Arg Leu Met Arg Glu Asn Tyr Asn Ile Thr Met Arg Val Trp
1585                1590                1595                1600
```

```
Leu Gly Leu Ser Gln His Ser Leu Asp Gln Ser Trp Ser Trp Leu Asp
            1605                1610                1615

Gly Leu Asp Val Thr Phe Val Lys Trp Glu Asn Lys Thr Lys Asp Gly
            1620                1625                1630

Asp Gly Lys Cys Ser Ile Leu Ile Ala Ser Asn Glu Thr Trp Arg Lys
        1635                1640                1645

Val His Cys Ser Arg Gly Tyr Ala Arg Ala Val Cys Lys Ile Pro Leu
    1650                1655                1660

Ser Pro Asp Tyr Thr Gly Ile Ala Ile Leu Phe Ala Val Leu Cys Leu
1665                1670                1675                1680

Leu Gly Leu Ile Ser Leu Ala Ile Trp Phe Leu Leu Gln Arg Ser His
            1685                1690                1695

Ile Arg Trp Thr Gly Phe Ser Ser Val Arg Tyr Glu His Gly Thr Asn
            1700                1705                1710

Glu Asp Glu Val Met Leu Pro Ser Phe His Asp
        1715                1720
```

DENDRITIC CELL RECEPTOR

CROSS REFERENCE TO RELATED APPLICATIONS

This application is a 371 of WO 97/45449.

FIELD OF THE INVENTION

This invention relates to dendritic cell receptors. In particular, it relates to human DEC-205, to the production and use thereof, and to ligands which bind to it. Human DEC-205 and its ligands are useful in prophylaxis and therapy.

BACKGROUND OF THE INVENTION

Dendritic cells perform important immunoregulatory functions by presenting antigens in the form of peptides bound to cell-surface major histocompatibility complex (MHC) molecules to T cells. Identification of the mechanism by which this antigen presentation function is achieved therefore has important implications in manipulating immune response in prophylaxis and therapy, particularly in humans.

Jiang et al, *Nature* 375: 151–155 (1995) disclose a murine dendritic cell receptor having a molecular weight of 205 kDa (murine DEC-205). However, they do not disclose a receptor on human dendritic cells.

The applicant has now identified a receptor on human dendritic cells. It is broadly to this receptor (likely to be the human homolog of murine DEC-205) that the present invention is directed.

SUMMARY OF THE INVENTION

The present invention has a number of aspects. In a first aspect, the invention provides isolated human DEC-205 which has an approximate molecular weight of 198–205 kDa and which includes the following amino acid sequences:

(i) TVDCNDNQPGAICYYSGNETEKEVK-
PVDSVKCPSPVLNTPWIPF QNCCYNFIITKN-
RHMATTQDEVQSTCEKLHPKSHILSIRDEKE
NNFVLEQLLYFNYMASWVMLGITYRNNSL
(amino acids at positions 1208–1323 of SEQ ID NO:1)
and (ii) SQHRLFHLHSQKCLGLDITKSVNELRMF-
SCDSSAML (amino acids at positions 71–106 of SEQ ID NO:1)

or a functionally equivalent fragment thereof.

In a further aspect, the invention provides isolated human DEC-205 which comprises the amino acid sequence shown in FIG. 11 or a functionally equivalent fragment thereof In a still further aspect, the invention provides isolated mature human DEC-205, which comprises the amino acids 27 to 1722 shown for human DEC-205 in FIG. 11.

In yet a further aspect, the invention provides an extracellular domain of human DEC-205 or a functionally-equivalent fragment thereof.

In a preferred embodiment, the extracellular domain fragment includes at least a portion of carbohydrate recognition domain (CRD7), spacer, and a portion of carbohydrate recognition domain (CRD8) of human DEC-205 (amino acids 1208 to 1323 of the amino acid sequence of FIG. 11).

In a still further aspect, the invention provides a polynucleotide encoding human DEC-205 or its extracellular domain as defined above. This polynucleotide is preferably DNA, more preferably cDNA, but can also be RNA.

In a specific embodiment, the polynucleotide coding for human DEC-205 includes the following nucleotide sequences (SEQ ID NOS:3& 4, respectively, in order of appearance):

```
(iii)  A ACA GTT GAT TGC AAT GAC AAT CAA CCA GGT GCT ATT TGC
       TAC TAT TCA GGA AAT GAG ACT GAA AAA GAG GTC AAA CCA GTT
       GAC AGT GTT AAA TGT CCA TCT CCT GTT CTA AAT ACT CCG TGG
       ATA CCA TTT CAG AAC TGT TGC TAC AAT TTC ATA ATA ACA AAG
       AAT AGG CAT ATG GCA ACA ACA CAG GAT GAA GTT CAT ACT AAA
       TGC CAG AAA CTG AAT CCA AAA TCA CAT ATT CTG AGT ATT CGA
       GAT GAA AAG GAG AAT AAC TTT GTT CTT GAG CAA CTG CTG TAC
       TTC AAT TAT ATG GCT TCA TGG GTC ATG TTA GGA ATA ACT TAT
       AGA AAT AAX TCT CTT;and (iv)   ATT AAT ATG CTG TGG AAG TGG GTG TCC CAG CAT CGG CTC TTT
       CAT TTG CAC TCC CAA AAG TGC CTT GGC CTC GAT ATT ACC AAA
       TCG GTA AAT GAG CTG AGA ATG TTC AGC TGT GAC TCC AGT GCC
       ATG CTG TGG TGG AAA TGC GAG CAC CA
``` where X is T or G.

In a further embodiment, the polynucleotide comprises part or all of the nucleotide sequence of FIG. 10.

In yet a further aspect, the invention provides a vector including a polynucleotide as defined above.

In still a flrter aspect, the invention provides a method of producing human DEC-205, the extracellular domain thereof or a fimctional fragment comprising the steps of:

(a) culturing a host cell which has been transformed or transfected with a vector as defined above to express the encoded human DEC-205, extracelhular domain or fragment; and (b) recovering the expressed human DEC-205, extracellular domain or fragment.

As yet an additional aspect, the invention provides a ligand that binds to human DEC-205 or its extracellular domain as defined above.

Preferably, the ligand is an antibody or antibody binding fragment or carbohydrate bearing protein.

The antibody or antibody binding fragment can be used in methods for extracting or isolating activated dendritic cells.

In still a further aspect, the invention provides a construct for use in therapy or prophylaxis. The construct will usually be a ligand-antigen construct or a DEC-205-antigen construct although ligand-toxin and DEC-205-toxin constructs are also contemplated. The ligand-antigen construct preferably consists of an antibody or antibody binding fragment which binds to human DEC-205 and a host-protective antigen. The DEC-205-antigen construct preferably consists of at least the extra-cellular domain of human DEC-205 and a host-protective antigen.

In yet further aspects, the invention contemplates methods of therapy or prophylaxis which employ human DEC-205, ligands or constructs containing them.

In yet a further aspect, the invention provides a molecule (hapten) which may be used to generate antibodies for identifying or puring human dendritic cells, which includes a peptide based upon part or all of the sequence of FIG. 11.

DESCRIPTION OF THE DRAWINGS

While the invention is broadly as defined above, it will be appreciated by those persons skilled in this art that it is not limited thereto and that it includes embodiments more particularly described below. It will also be better understood by reference to the accompanying drawings, in which.

Figure 4:
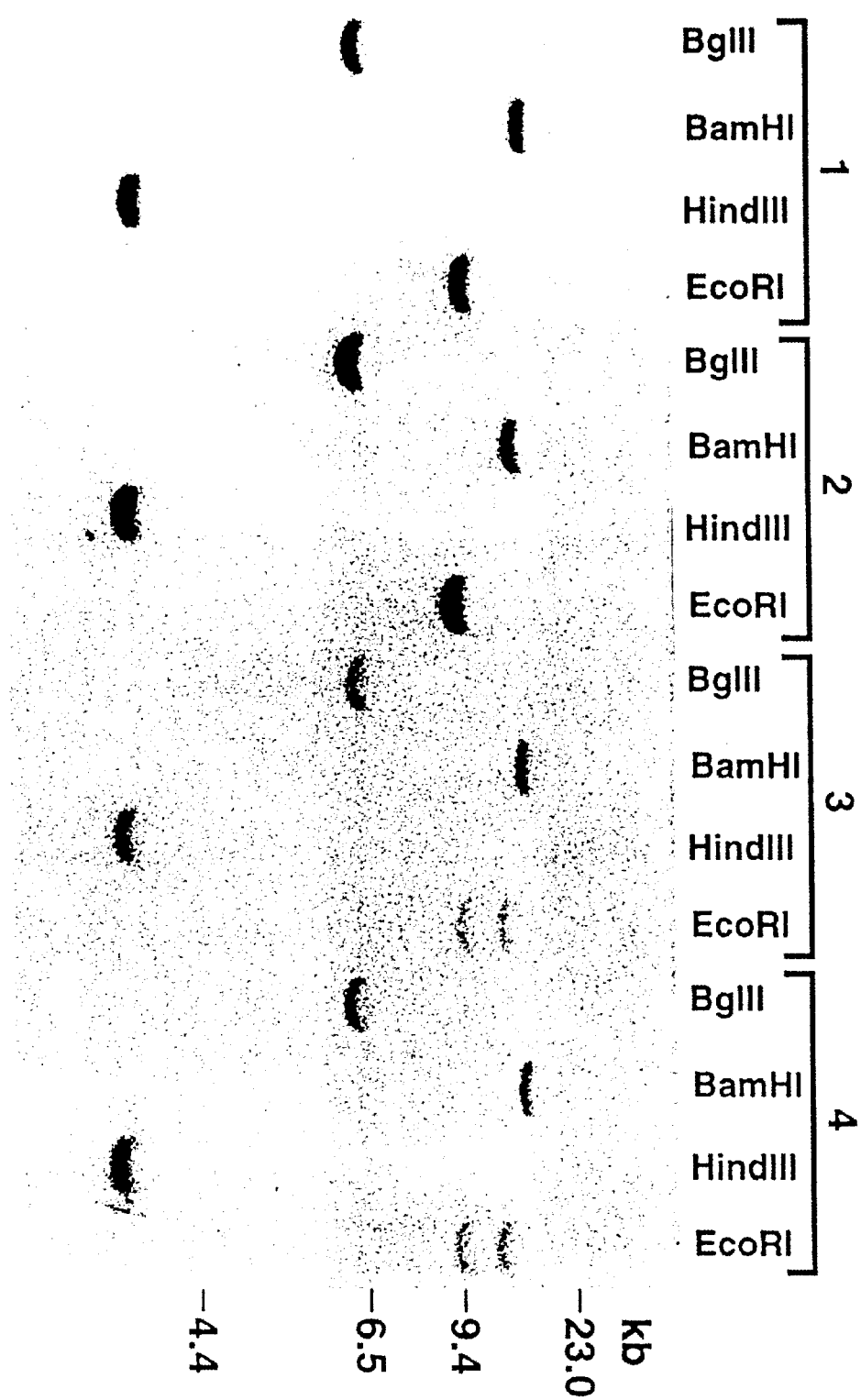
Figure 5:
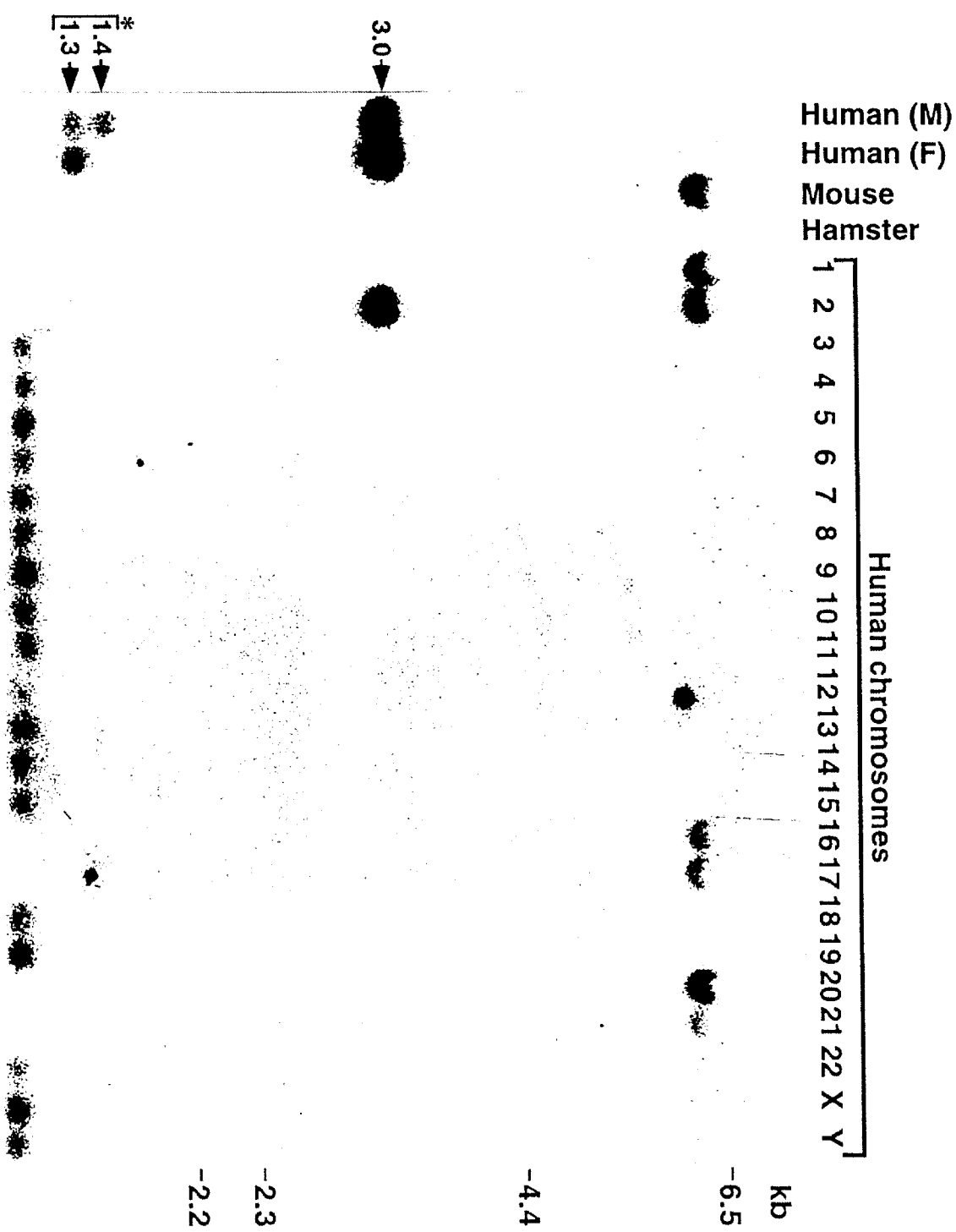
Figure 6:
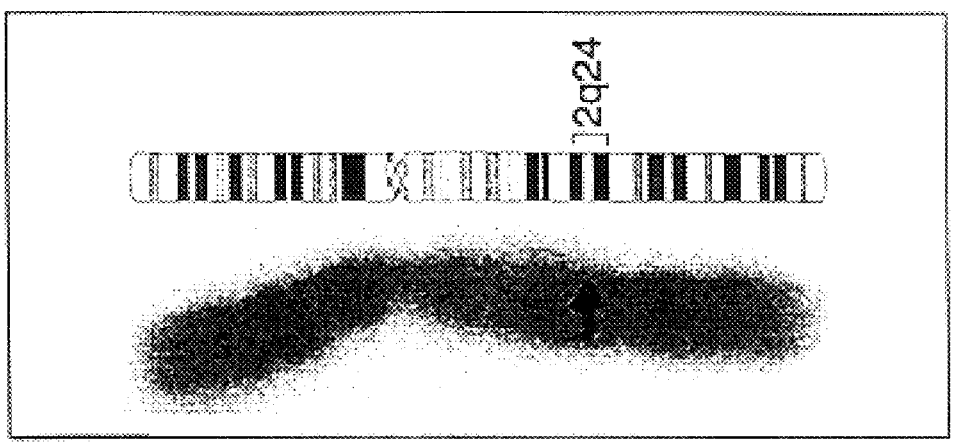
Figure 6:
Figure 7:
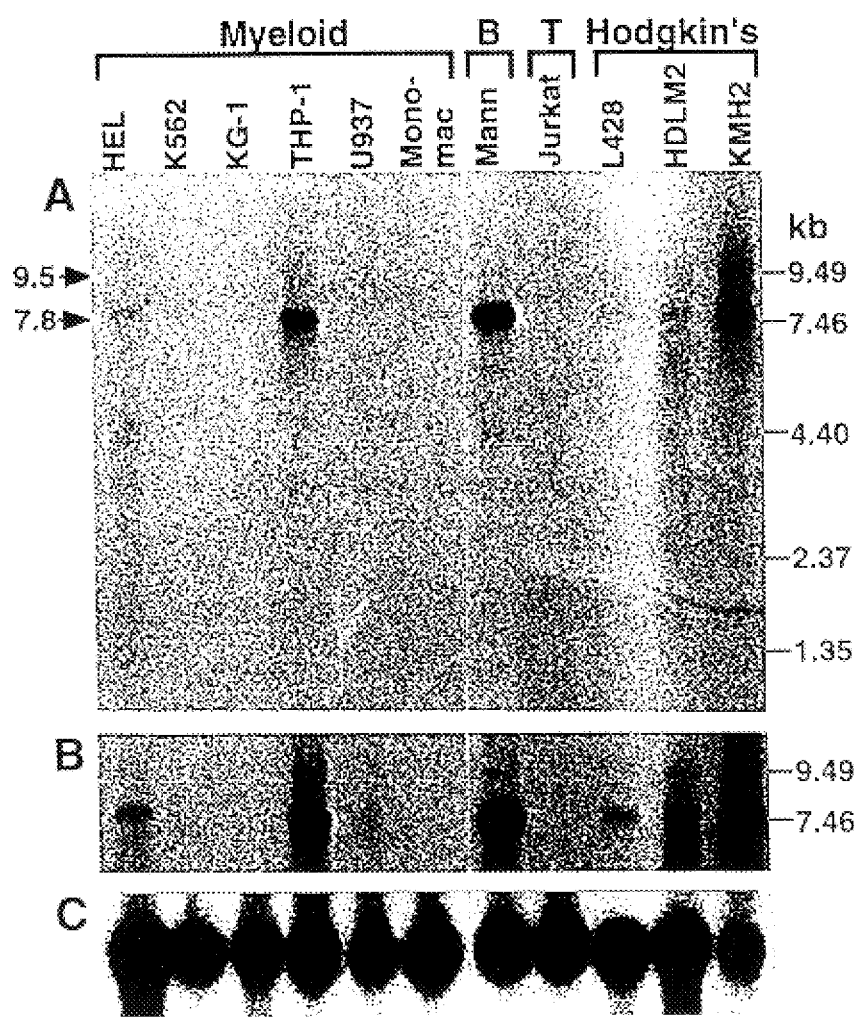
Figure 8:
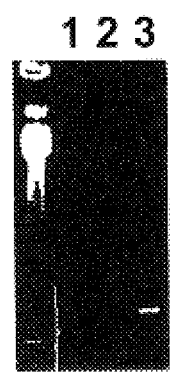

A. The predicted amino acid sequence of human DEC-205 (SEQ ID NO:1) is aligned with the mouse homolog (SEQ ID NO:31). The regions corresponding to DEC-205 domain structure are bracketed. The positions of amino acids are shaded where there are identical or conservatively replaced amino acids between the sequences, and the asterisks indicates conserved cysteines. The diamonds indicates potential N-glycosylation sites conserved between the sequences. The arrow indicates one amino acid deletion in CRD-5 of human DEC-205. The circles indicate conserved potential serine-phosphorylation sites by protein kinase C (open circle) or casein kinase (closed circle). B. The % identity between human and mouse DEC-205 is indicated above each domain (boxed, See FIG. 2A for key);

FIG. 4 shows that human DEC-205 is probably a one-copy gene. Genomic DNA isolated from the peripheral blood of four individuals was digested with the restriction enzymes BgIII, BamHI, HindIII or EcoRI and subjected to Southern blot analysis with the [$^{32}$P]cysteine-rich domain probe. The final wash was 0.3×SSC at 65° C. The positions of the DNA molecular size standards are indicated to the right;

FIG. 5 shows that human DEC-205 gene localizes on chromosome 2. A somatic cell hybrid panel blot (restriction-digested with PstI) was subjected to Southern blot analysis with the [$^{32}$P]cysteine-rich domain probe. The final wash was 0.3×SSC at 65° C. The positions of the DNA molecular size standards are indicated to the right. The estimated molecular size of the probe-specific bands are indicated to the left. The asterisk indicates weakly hybridized bands. M, male; F, female;

FIG. 6 shows that human DEC-205 gene maps to chromosome band 2q24. A. A metaphase spread of human chromosomes were subjected to fluorescent in situ hybridization (FISH) with 6.6 kb human DEC-205 cDNA probe. The final wash was 0.1×SSC at 60° C. The FISH image was overlaid with a DAPI-stained chromosome image. The DEC-205 specific signals are indicated by the arrowheads. B. An inverted image of chromosome 2 containing DEC-205-specific signal (see FIG. 6A) is aligned with an ideogram of chromosome 2. The chromosome band corresponding to DEC-205 gene is indicated to the right;

FIG. 7 shows that expression of DEC-205 transcripts within human hematopoetic cell lines. Total RNA prepared from the cell lines were subjected to Northern blot analysis with the [$^{32}$P]fragment 3 (A and B), or [$^{32}$P]-actin (C) probes. The final wash was 0.1×SSC at 65° C. The positions of the RNA molecular size standards are indicated to the right. The estimated molecular size of DEC-205 transcripts are indicated to the left. A, 24 h exposure; B, 72 h exposure;

FIG. 8 shows RT-PCR analysis of DEC-205 mRNA in human DC preparations. Specific product is seen using lineage negative; fresh DC (lane 2) and a stronger signal with CMRF44$^+$ low density cultured DC (lane 3). CD8$^+$ T lymphocytes (lane 1) contain no DEC-205 mRNA Ethidium stain.

Figure 9:
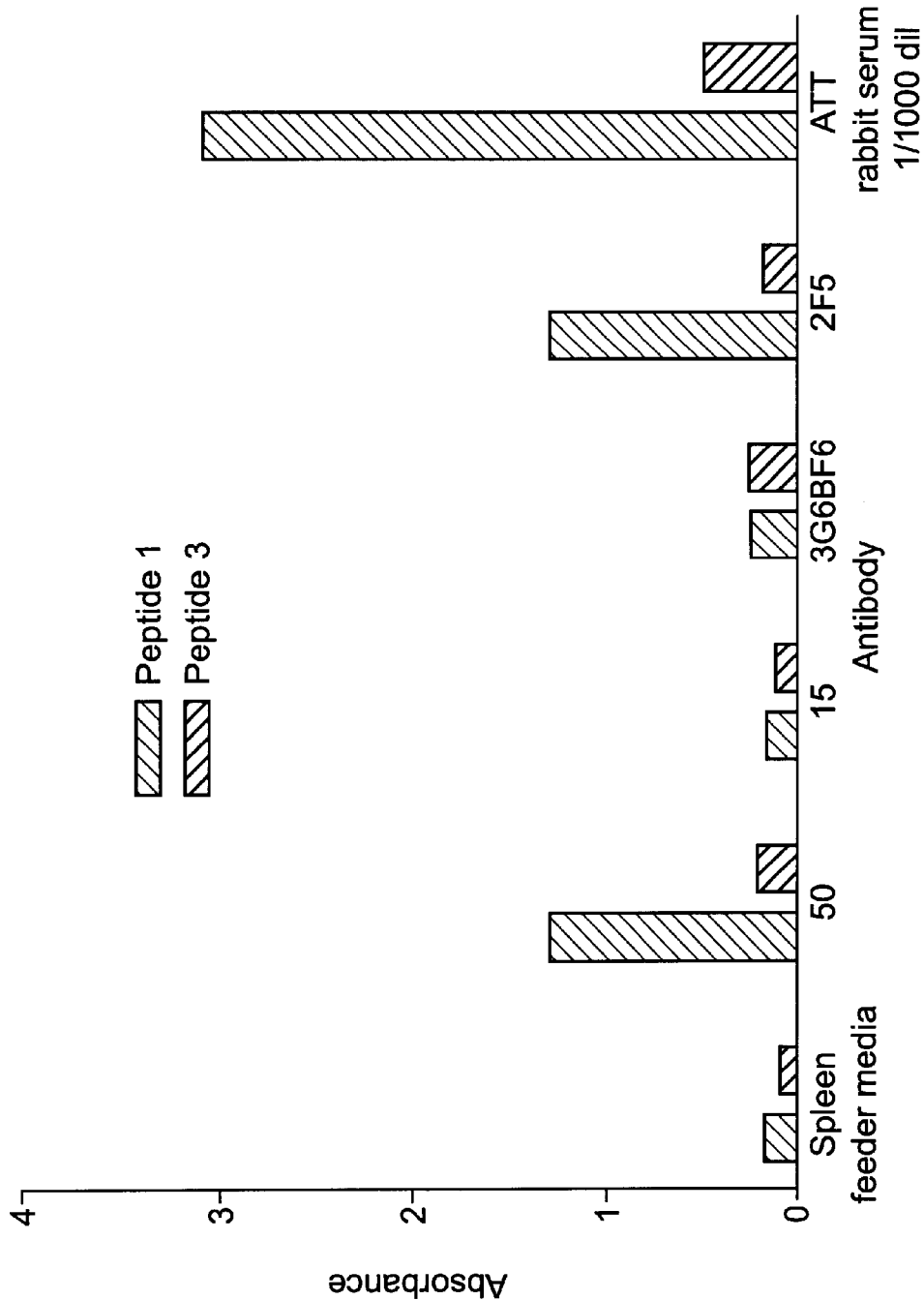

FIG. 9 represents the result of an ELISA assay showing a monoclonal antibody binding specifically to DEC-205 peptide 1 and not peptide 3. Positive control binding of a hyperimmunized rabbit anti-DEC-205-peptide 1 serum and hyperimmunized rabbit anti-DEC-205-peptide 2 serum are shown;

FIG. 10 gives the DNA sequence (SEQ ID NO:1) for human DEC-205 (coding region only);

FIG. 11 gives the human DEC-205 amino acid sequence (SEQ ID NO:2).

DETAILED DESCRIPTION OF THE INVENTION

A. Human DEC-205

Figure 1:
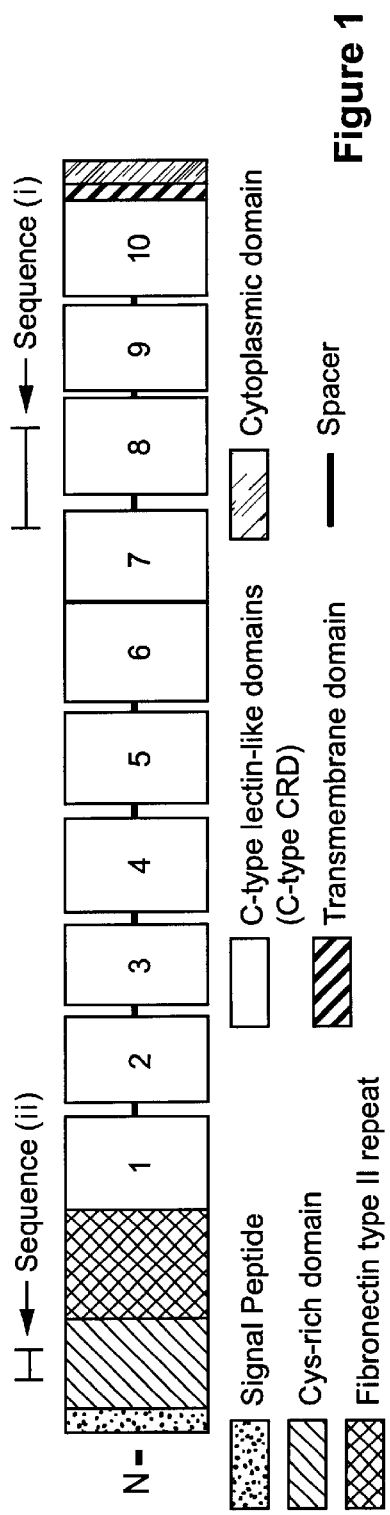
FIG. 1 shows the structure of human DEC-205.

The human DEC-205 of the invention is believed to be the human homolog of murine DEC-205 and has an approximate molecular weight of 198 to 205 kDa. It has the structure shown in FIGS. 1 and 2A. It also has the deduced amino acid sequence shown in FIG. 11.

Human DEC-205 can usefully be provided in a number of different forms. These include human DEC-205 itself the "mature" form of human DEC-205, and the extracellular receptor domain of human DEC-205.

The "mature" form of human DEC-205 of the invention is human DEC-205 less its native amino-terminus leader or signal sequence, whereas the extracellular receptor domain is human DEC-205 lacking the signal sequence, the transmembrane region and cytoplasmic domain (where present).

The extracellular domain may be identified through commonly recognised criteria of extracellular amino acid sequences. The determination of appropriate criteria is known to those skilled in the at, and has been described, for example by Hopp et al., *Proc. Natl. Acad. Sci. USA* 78, 3824–3828 (1991); Kyte et al., *J. Mol. Biol.* 157 105–132 (1982); Emini, *J. Virol* 55, 836–839 (1985); Jameson et al. *CA BIOS* 4 181–186 (1988); and Karplus et al. *Naturwissenschaften* 72, 212–213 (1985). Amino acid domains predicted by these criteria to be surface exposed. are characteristic of extracellular domains.

The amino acid sequences of the predicted regions for human DEC-205 are shown in FIG. 3A. These include the amino acid sequences for the signal peptide, cysteine-rich domain, fibronectin type II domain, Carbohydrate Recognition Domain-1, (CRD-1), CRD-2, CRD-3, CRD-4, CRD-5. CRD-6, CRD-7, CRD-8, CRD-9, CRD-10, transmembrane domain and cytoplasmic domain.

Human DEC-205 of the invention or its extracellular receptor domain (or parts thereof) may be prepared by methods known in the art. Such methods include protein synthesis from individual amino acids as described by Stuart and Young in "Solid Phase Peptide Synthesis", Second Edition, Pierce Chemical Company (1984). It is however preferred that human DEC-205 and/or its extracellular receptor domain or parts thereof be prepared by recombinant methods as will be detailed hereinafter.

Example 1 provides further details of human DEC-205.

EXAMPLE 1

Langerhans cells were prepared from human skin. Epidermal cell suspensions were prepared from split thickness normal human breast skin by 30 min dispase (Boehringer-Mannheir, Mannheim, Germany; 0.5% in PBS) treatment at 37° C., followed by 10 min disaggregation in the presence of trypsin (0.25% in PBS), DNase I (5U/ml in PBS) and 5 mM EDTA at room temperature. Langerhans cells were then enriched by Ficoll/Metrizoate gradient separation (d=1.077g/cm³). Final cell suspensions contained 3–15% Langerhans cells as determined by HLA-DR positivity. Total RNA was extracted using Trizol reagent according to the manufacturer's instructions.

Degenerate primers were prepared on an Applied Biosystems DNA Synthesizer with the primer sequences (d) and (e) as set out below (SEQ ID NOS:5 & 6, respectively, in order of appearance):

(d) 5'-GAX ACY GAX GGY TTX TGG AA-3'

(e) 3'-GCY GTX TTZ TCZ AAC CAC AT-5' wherein X is C or T, Y is A, C, G or T, and Z is G or A.

Single stranded cDNA was prepared using total RNA and reverse transcribed by AMV reverse transcriptase using the 3' primer (e). Subsequently, the cDNA was amplified using the 5'(d) and 3'(e) primer using PCR amplification according to techniques known in the art.

The amplified products were run on a 2% agarose gel and visualized with ethidium bromide staining.

The DNA was purified and ligated into the T tailed pGEM vector (available from Promega) using standard techniques.

The ligation mixture was transformed into competent *E. coli* JM 109 bacteria (available from Promega) which were grown on agar plates with appropriate antibiotic selection. Two colonies were isolated. DNA was prepared and digested with restriction enzymes. Two inserts of the same size as the PCR product were sequenced by double-stranded DNA sequencing techniques using a Sequence Kit (Sequence 2.0 USB Lab Supply, Pierce). The two clones corresponded to human DEC-205.

The amino acid sequence of human DEC-205 was determined to include the following amino acid sequences (portions of SEQ ID NO:1):

(i) TVDCNDNQPGAICYYSGNETEKEVK-PVDSVKCPSPVLNTPWIPF QNCCYNFIITKN-RHMATTQDEVQSTCEKLHPKSHILSIRDEKE NNFVLEQLLYFNYMASWVMLGITYRNNSL; and (ii) SQHRLFHLHSQKCLGLDITKSVNELRMF-SCDSSAML.

Determination of these sequences was fundamental to isolating the cDNA for human DEC-205 detailed below.

In the partial sequences given above, individual amino acids are represented by the single letter code as follows:

| Amino Acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic Acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Unidentified | | X |

This code also applies to the predicted full sequence of FIG. 11, deduced from the cDNA encoding human DEC-205 isolated as described below.

B. Polynucleotides Encoding Human DEC-205

In another aspect of this invention, the applicants provide polynucleotides encoding human DEC-205 or its extracellular domain. These polynucleotides may be DNA (isolated from nature, synthesised or cDNA) or RNA. Most often, the polynucleotides will be DNA.

The polynucleotides of the invention specifically include those which include the nucleotides (SEQ ID NOS 3 & 4, respectively, in order of appearance)

(iii) A ACA GTT GAT TGC AAT GAC AAT CAA CCA GGT GCT ATT TGC

TAC TAT TCA GGA AAT GAG ACT GAA AAA GAG GTC AAA CCA GTT

GAC AGT GTT AAA TGT CCA TCT CCT GTT CTA AAT ACT CCG TGG

ATA CCA TTT CAG AAC TGT TGC TAC AAT TTC ATA ATA ACA AAG

AAT AGG CAT ATG GCA ACA ACA CAG GAT GAA GTT CAT ACT AAA

TGC CAG AAA CTG AAT CCA AAA TCA CAT ATT CTG AGT ATT CGA

GAT GAA AAG GAG AAT AAC TTT GTT CTT GAG CAA CTG CTG TAC

TTC AAT TAT ATG GCT TCA TGG GTC ATG TTA GGA ATA ACT TAT

AGA AAT AAX TCT CTT; and (iv) ATT AAT ATG CTG TGG AAG TGG GTG TCC CAG CAT CGG CTC TTT

CAT TTG CAC TCC CAA AAG TGC CTT GGC CTC GAT ATT ACC AAA

TCG GTA AAT GAG CTG AGA ATG TTC AGC TGT GAC TCC AGT GCC

ATG CTG TGG TGG AAA TGC GAG CAC CA where X is T or G,
as well as the full nucleotide sequence shown in FIG. 10, but are not limited thereto.

The invention also includes within its scope functional equivalents of these polynucleotides.

This aspect of the invention will now be illustrated by the following Examples.

EXAMPLE 2

EXPERIMENTAL PROCEDURES

Cell culture—The cell lines, HEL, K562, KG-1, THP-1, U937, Mann and Jurkat were obtained from the American Type Culture Collection (Rockville, Md.). L428 cells were provided by V. Diehl (Klinik for lnnere Medizin, Cologne, Germany). HDLM2 and KMH2 cells were obtained from the German Collection of Micro-organisms and Cell Culture (Braunscfweig, Germany). Mono Mac 6 cells (Bufler et al (1995) *Eur. J. Immunol.* 25, 604–610) were provided by H. Engelmann (Institute for Immunology, Munchen, Germany). All cell lines were maintained in RPMI 1640, 10% fetal calf serum, 100 U/ml penicillin, 100 ug/ml streptomycin except that HDLM2 cells were with 20% fetal calf serum.

Isolation of Leukocytes—Leukocyte populations were isolated using standard laboratory procedures.

Figure 2A:
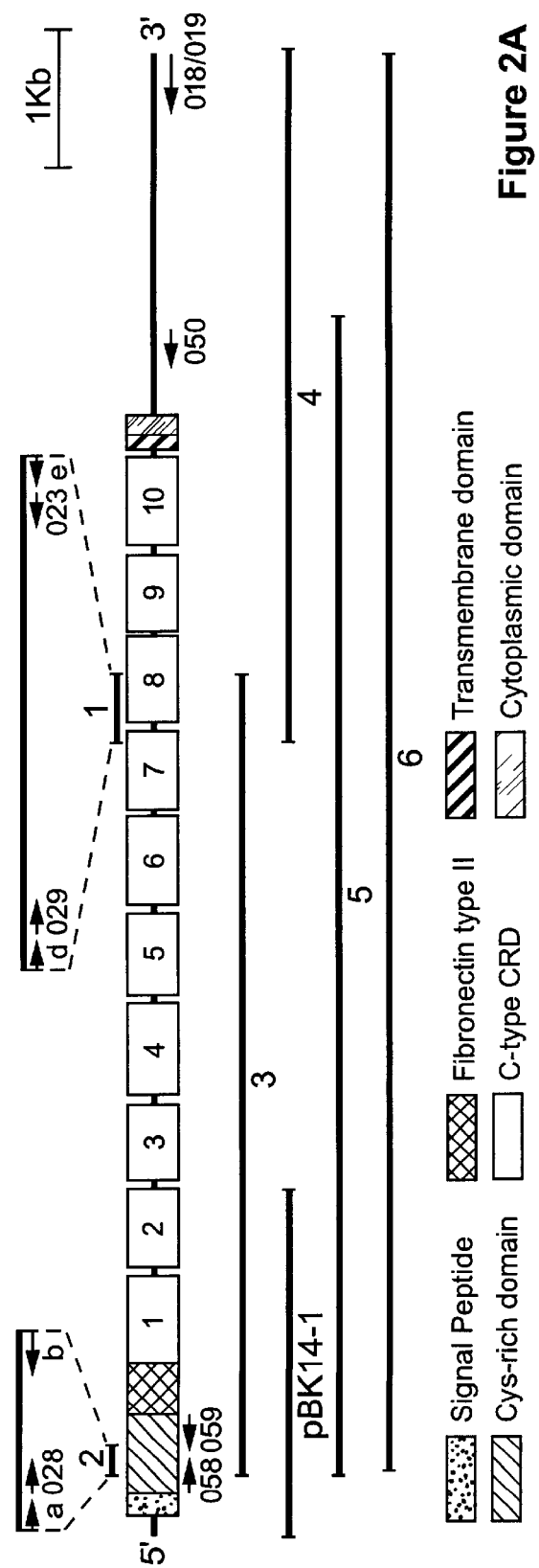
FIG. 2 shows the strategy for isolation of human DEC-205 cDNA. A. A schematic presentation of human DEC-205 mRNA with the regions corresponding to DEC-205 domains. The positions of the primers used for the cDNA cloning and analysis are indicated with arrows. The positions of reverse transcriptase-polymerase chain reaction (RT-PCR) fragments 1 to 6 and the clone pBK14-1 are indicated with bars: B. RT-PCR amplification of fragment 1 and 2 from L428 and HEL cell line RNA. L428 and HEL cells were subjected to RT-PCR with two pairs of degenerate primers (DEC-a/-b, and DEC-d/-e), fractionated by electrophoresis through 2% agarose gel, and stained with ethidium bromide. C. RT-PCR and 3'-RACE amplification of fragment 3 and 4 from L428 cells using the primers 028/023 and 029/019, respectively. A cDNA pool of L428 cells was subjected to 3'-RACE and RT-PCR, electrophoresed through 0.8% agarose gel, and stained with ethidium bromide. The numbers on the top correspond to the name of fragment in FIG. 2A. The positions of DNA molecular size standard are indicates to the right. The estimated molecular size of the RT-PCR products are indicated to the left.

Isolation of cDNA encoding for human DEC-205—A set of degenerate oligonucleotide primers were designed based on the published amino acid sequence of mouse DEC-205 (Jiang etal (1995), above) and synthesized in house or by Life Technologies (Auckland, New Zealand) (see FIG. 2A). These primers were (SEQ ID NOS:7–10 respectively, in order of appearance)

DEC-a (5'-AAYATGCTNTGGAARTGGGT-3'),
DEC-b (5'-TGRTGYTCRCAYTTCCACCA-3'),
DEC-d (5'-GAYACNGAYGGNTTYTGGAA-3') and
DEC-e (5'-GCNGTYTTRTCRAACCACAT-3'), where Y=C or T, R=A or G, N=A or C or G or T. Total RNA isolated from L428 or HEL cells was reverse transcribed with avian myeloblastosis virus reverse transcriptase (Promega, Madison, Wis.) at 55° C. for 1 h using the primers DEC-b or DEC-e. PCR was performed using the resultant cDNA and Taq polymerase (Boebrunger Mannheim, Auckland, New Zealand) with the primers DEC-a/-b for DEC-b-primed or DEC-d/-e for DEC-e-primed cDNAs. The PCR conditions used were the initial denaturation at 94° C. for 5 min, 35 cycles of denaturation at 94° C. for 1 min, annealing at 54° C. for 1 min, extension at 72° C. for 1 min, and the final extension at 72° C. for 5 min. The PCR reactions were fractionated with 2% agarose gel in 40 mM Tris-acetate, pH 8.3, 1 mM EDTA (TAE) buffer, and stained with 0.5 ug/ml ethidium bromide. The PCR fragments (fragment 1 and 2, see FIG. 2A and 2B) were cloned into pGEM-T vector (Promega), and sequenced manually using Sequenase DNA sequencing kit (Amersham Life Science, Auckland, New Zealand).

A set of oligonucleotide primers nested within the DNA sequence of fragment 1 and 2 were synthesized (see FIG. 2A). These primers were (SEQ ID NOS:11–13, respectively, in order of appearance):

023(5'-GCTCTAGAAACATGACCCATGAAGCC-3' containing a XbaI site),
028(5'-GCTCTAGACATCGGCTCTTTCATTTGT-3' containing a XbaI site) and.
029(5'-CGGGATTCACAGTTGATTGCAATGACA-3' containing a EcoRI site)

where incorporated restriction sites are underlined. Two ug of poly(A) RNA from L428 cells was reverse transcribed with 200 U of SuperScriptII (Life Technologies) at 45° C. for 1 h using an oligo d(T) adaptor primer (SEQ ID NO:14)

018(5'-GACTAGTCTGCAGAATTCTTTTTTTTTTTTTT TT-3', containing a SpeI, PstI, and EcoRI sites). After heat-inactivation at 70° C. for 15 min, the reaction was incubated with 1 U RNaseH (Life Technologies) at 37° C. for 30 min, heat-inactivated at 70° C. for 15 min, and diluted to 1 ml with 10 mM Tris-HCI, pH 8.0,1 mM EDTA (L428 cDNA pool). In order to isolate the fragment 3 (connecting the fragment 1 and 2) (see FIG. 2A), PCR was performed with 5 ul of L428 cDNA pool, the primers 028 and 023, and 2.5 U of Expand enzyme mix (Boehringer Mannheim). The PCR conditions were the initial denaturation at 94° C. for 2 min, 10 cycles of 10 cycles of denaturation at 94° C. for 15 sec, annealing at 53° C. for 30 sec, and extension at 68° C. for 4 min, followed by 20 cycles of denaturation at 94° C. for 15 sec. annealing at 53° C. for 30 sec, and extension at 68° C. for 4 min plus additional 20 sec for each cycle, and the final extension at 68° C. for 15 min. 3'-rapid amplification of cDNA ends (3'-RACE) (Frohman et al (1988) *Proc. Natl. Acad. Sci. USA* 85, 8998–9002) was performed in order to isolate the fragment 4 (connecting the fragment 1 and the 3'-untranslated region of DEC-205) (see FIG. 2A). PCR was performed with 5 ul of L428 cDNA pool and the primer 029 and an adaptor primer 019 (SEQ ID NO:15) (5'-GACTAGTCTGCAGAATTC, containing a SpeI, PstI and EcoRI site), in the same conditions for the fragment 3. The PCR reactions were fractionated with 0.8% agarose gel in TAE buffer, and stained with ethidium bromide. Both the fragment.3 and 4 were restriction digested with XbaI and EcoRI, respectively, and cloned into pBluescript 11 (Stratagene, La Jolla, Calif.). The representative clones from the fragment 3 (pB38fl) and 4 (pb30-3) were sequenced with a LI-COR automated sequencer (LI-COR, Lincoln, Neb.) using SequiTherm cycle sequencing kit (Epicentre Technologies, Madison, Wis.). If required, these plasmids were subjected to exonucleaseIII-nested deletion using Erase-A-Base system (Promega), and used for sequencing.

An oligo dT-primed L428 cDNA library was prepared using ZAP Express cDNA Gigapack Cloning kit (Stratagene) according to manufacturers instruction. The fragment 3 was labeled with [α-32P]dCTP (NEN) using Multiprime system (Amersham Life Science). The library was screened by plaque hybridization with the [$^{32}$P] fragment 3 using standard techniques (Sambrook, J., Fritsch, E. F., and Maniatis, T. (1989) *Molecular Cloning. A Laboratory Manual*, 2Ed., Cold Spring Harbour Laboratory, New York, USA). The specific activity of the probe was 0.8×10$^9$ cpm/ug DNA and used at 1×10$^6$ cpml/ml. The final wash was in 0.1×SSC, 0.5% SDS at 65° C. (1×SSC is 0.15 M NaCl, 15 mMM Na-citrate, pH7.0). Positive clones were converted to phagemid pBK-CMV (Stratagene) and sequenced using an automated sequencer.

In order to verify the DNA sequence obtained from the PCR clones, pB38f for fragment 3 and pB30-3 for fragment 4, the fragment 5 was PCR-amplified from a L428 cDNA pool using primers 058 (SEQ ID NO:16) (5'-CGGGATCCCTCTGGCCGCGCACTAATGA-3' containing a BamHl site) and 050 (SEQ ID NO:17)(5'-CCGCTCGAGCTGTGGATACCAGCACATGCCT-3' containing a XhoI site) (see FIG. 2A). The PCR conditions were identical to that for the fragment 3 except using longer extension period (6 min) for cycling. The fragment 5 was sequenced directly using the IRD$_{40}$-labeled custom primers (MWG-Biotech, Ebersberg, Germany) and a LI-COR automated sequencer without cloning. These primers were (SEQ ID NOS:18–25, respectively, in order of appearance): IRD001 (5'-GATGGGAACTCTTATGGGAGACCT-3' at nucleotide 523–555), IRD002 (5'-TGATGCAGGCTGGCTGCCAAATAA-3' at nucleotide 1134–1157), IRD003 (5'-AACTGGGCAACTGTTGGTGGAAGA-3' at nucleotide 1759–1782), IRD004 (5'-ATGGCGAAGAGGCTGGCATTTCTA-3' at nucleotide 2334–2357), IRD005 (5'-CTCAAGCAAGCGATACCTGTCACT-3' at nucleotide 2972–2995), IRD006 (5'-TGGGCAACTCGAAGACTGTGTAGT-3' at nucleotide 3624–3647), IRD007 (5'-CACCAGCACAGCATTCTTGCTTGT-3' at nucleotide 4168–4191) and IRD008 (5'ATTTGTGAGCAGACTGATGAGGGA-3' at nucleotide 4797–4820). The sequences of these primers were based on those of pb38fl and pb30-3, and they were positioned as 540–650 bp apart, ensuring the generation of contigs overlapping by at least 100 bp after automated sequencing.

Southern Blot Analysis—Genomic DNA was prepared from peripheral blood of patients with hematological disorders (each patient was karyotyped at Canterbury Health Laboratories, Christchurch, New Zealand). Approximately 8 ug of genomic DNA was digested with BgIII, BamHI, EcoRI, or HindIII, fractionated in 0.8% agarose gel in 89 mM Tris-borate, pH 8.3, 2 mM EDTA, and transferred to Hybond N+ by capillary reaction. A PCR-fragment corresponding to the cyteine-rich domain was PCR-amplified from pBK14-1 using the primers 058 and 059 (SEQ ID NO:26) (5'-CGGAATTCGATCTCATGATAAGGCTGGTCACA-3' containing a EcoRI site) (see FIG. 2A). Briefly, PCR was performed with 2 ng of pBK14-1, the primer 058 and 059, and Taq polymerase. The PCR conditions used were the initial denaturation at 94° C. for 2 min, 30 cycles of denaturation at 94° C. for 15 sec, annealing at 55° C. for 15 sec. extension at 72° C. for 30 sec, and the final extension at 72° C. for 5 min. The 450 bp PCR product was labeled with [α-$^{32}$P]dCTP using Multiprime labeling system (Amersham Life Science). The blot was hybridized with the probe using standard technique (Sambrook et al, (1989), above). The specific activity of the probe was 0.8×10$^9$ cpm/ug DNA and used at 1×10$^6$ cpm/ml. The final wash was in 0.3×SSC, 0.5% SDS at 65° C., and exposed to X-OMAT AR film (Kodak) with an intensifying screen at −70° C.

A blot containing PstI-digested genomic DNA from a human-rodent somatic hybrid cell panel was obtained from Oncor (Gaithersburg, Md.), and probed with the [$^{32}$P] cysteine-rich domain fragment as described above.

Fluorescent in Situ Hybridization—Metaphase spreads were prepared from phytohaemagluttinin-stimulated peripheral blood lymphocytes of a 46,XY male donor using standard cytogenetic procedures. The fragment 6 was amplified by recombinant PCR with the fragment 3 and 4 (see FIG. 2A). PCR was performed with each of the fragment 3 and 4 and the primers 028 and 019 in the same conditions for the fragment 3 except using longer extension period (7 min) for cycling. The fragment 6 was labelled with biotin-14-dCTP using a BioPrime random prime labelling kit (Bethesda Research Laboratories, Gathersberg, Md.), and hybridized to metaphase cells on slides. Conditions for hybridization and immununofluorescent detection were essentially as described (Morris et al, (1993) *Human Genetics*, 91, 31–36), except that Cot 1 suppression was not required, slides were washed to a stringency of 0.1×SSC, 60° C. after hybridization, and an additional amplification step was needed because of the small size of the probe. For precise chromosome band localization, DAPI and FITC images were captured separately for each metaphase from the fluorescent microscope to computer using a Photometrics KAF1400 CCD camera and IPLAB Spectrum software (Signal Analytics, Va.), and colour-joined using Multiprobe extension software.

Northern Blot Analysis—Approximately 10 ug of total RNA from cultured cells were fractionated in formaldehyde-denatured 1% agarose gel and transferred to Hybond N+ (Amersham) using 3 M NaCl, 8 mM NaOH, 2 mM sarkosyl with Turboblotter (Schleicher & Schuell, Keene, N.H.) for 3 h. The membrane was UV-crosslinked (Stratalinker, Stratagene), and hybridized with [$^{32}$P]fragment 3 or [$^{32}$P] human §-actin probe using standard techniques (Sambrook et al (1989), above). The specific activity of the probes were 0.9–1.1×10$^9$ cpm/ug DNA and used at 0.7–1.1×10$^6$ cpm/ml. The final wash was in 0.1×SSC, 0.5% SDS at 68° C., and exposed to X-OMAT AR film (Kodak) with intensifying screen at −70° C.

Reverse Transcription-PCR Analysis—Total RNA from isolated leukocytes was incubated with RNase-free DNaseI (Life Technologies), and was reverse transcribed using SuperscriptII with the oligo dT adaptor primer 018. PCR was performed using a pair of DEC-205 specific primers 060 (SEQ ID NO:27) (GTGGATCCAGTACAAGGGTCA at nucleotide 4655–4686) and 056 (SEQ ID NO:28) (ACCAAATCAGTCCGCCCATGA at nucleotide 5116–5096) with Taq polymerase in the presence of a PCR additive, Q buffer (Qiagen) by touch down PCR (Don, R. H., Cox, P. T., Wainwright, B. J., Baker, K., and Mattick, J. S., (1991) *Nucleic Acid Res.* 19, 4008). PCR conditions used were the initial denaturation at 92° C. for 2 min, 21 cycles of denaturation at 9220 C. for 15 sec, annealing at 60° C. minus 0.5° C./cycle for 15 sec, extension at 68° C. for 30 sec, 15 cycles of denaturation at 92° C., annealing at 50° C., extension at 68° C. for 1 min and the final extension at 68° C. for 5 min. Human glycelaldehyde-3-phosphate dehydrogenase (GAPDH) (Tokunaga, K., Nakamura, Y., Sakata, K., Fujimori, K., Ohkubo, M., Sawada, K., and Sakiyama, S. (1987) *Cancer Res.* 47, 5616–5619) was used for normalization. The primers for GAPDH were 053 (SEQ ID NO:29) (ATGGGGAAGGTGAAGGTCGGA-3' at nucleotide 61–81), and 055 (SEQ ID NO: 30) (AGGGGCCATCCACAGTCTTCT-3' at nucleotide 634–614). The PCR reactions were fractionated with 1.5 % agarose gel in TAE buffer, and stained with 0.5 ug/ml ethidium bromide.

Sequence Data Analysis

The National Center of Biotechnology Information (NCBI) Center electronic mail server BLAST was used to search for homologous sequences. Sequence alignments and motif search were done using Bestfit and Motifs programs, respectively, of GCG computer package (Madison, Wis.).

RESULTS

Figures 2B, 2C:
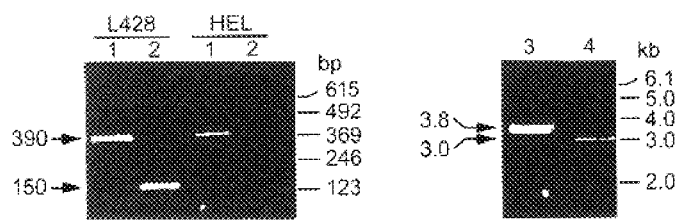

Isolation of CDNA for human DEC-205. —Based on the amino acid sequence of mouse DEC-205, a set of degenerate primers were synthesized and used to perform RT-PCR using the Hodgkin's disease-derived L428 cell line and the myeloid HEL cell lines (FIG. 2). The two pair of primers (DEC-d/-e, and DEC-a/-b) gave rise to the specific RT-PCR products, fragment 1 (390 bp) and 2 (150 bp), respectively (FIG. 2A and 2B). These specific fragments were cloned and sequenced (data not shown). The deduced amino acid sequences of fragment 1 and 2 were ~80% identical to that of mouse DEC-205, indicating that these fragments were derived from the cDNA of human DEC-205.

Primers nested within these fragments were synthesized and further RT-PCR and 3'-RACE performed using a L428 cDNA pool reverse transcribed with an oligo dT adapter primer 018. A 3.8 kb RT-PCR product (fragment 3) was obtained using primer 028 and 023 (FIG. 2A and 2C). A 3.2 kb 3'-RACE product (fragment 4) was obtained using primer 029 and an adaptor primer 019 (FIG. 2A and 2C). The fragment 3 was cloned and several identical clones were identified by restriction enzyme map analysis (data not shown), and one of which, pb38fl, was fully sequenced: The DNA sequence of the fragment 3 (pB38fl) extending from the middle of cysteine-rich domain to the middle of CRD-8 (FIG. 2A), was 82% identical to the published mouse DEC-205 cDNA sequence. The fragment 4 was cloned and two distinct clones identified by restriction enzyme map analysis. Both clones were partially sequenced and the 3' end DNA sequence of one clone (eg. pb30-3) was found to contain a poly A tail and with 72% identical to 3'-untranslated region of mouse DEC-205 (data not shown). Therefore, the pb30-3 was sequenced to obtain the DNA sequence of the coding region of DEC-205 plus partial 3'-untranslated region. The resulting DNA sequence for the coding region was ~80% identical to that of mouse DEC-205 spanning from the middle of CRD-8 to the end of cytoplasmic domain (FIG. 2A). The DNA sequences obtained from pb38fl and pb30-3 overlapped by 320 bp, covering 95% of human DEC-205 coding region.

In order to complete the 5' end of the DEC-205 cDNA sequences a L428 cDNA library was screened by plaque hybridization using $^{32}$P-labeled fragment 3 as a probe. A clone (pBKI4-1) was isolated, and the 1.5 kb insert of this clone was sequenced (FIG. 2A). The sequence was 18 80% identical to the mouse sequence and corresponded to the signal peptide, cysteine-rich domain, fibronectin type II domain, CRD-1 and part of the CRD-2. The pBK14-1 contained 51 bp 5'-untranslated region, and overlapped with fragment 3 by ~1.2 kb.

To validate the DNA sequence obtained from the PCR clones, a further RT-PCR fragment (fragment 5) amplified with primers 058 (nested in the cysteine-rich domain) and 050 (located ~130 bp downstream of the stop codon) was prepared (FIG. 2A). The fragment 5 PCR product was sequenced directly using MRD$_{41}$-labeled custom primers without cloning. A total of 10 point mutations, presumably generated because of the low fidelity of thermostable polymerases were found and corrected in the PCR clone-derived DNA sequence. The complete cDNA sequence for human DEC-205 is 5166 bp in size, and encodes for a predicted 198 kDa type I transmembrane protein with 1722 amino acids before post translational modification.

Figure 3B:
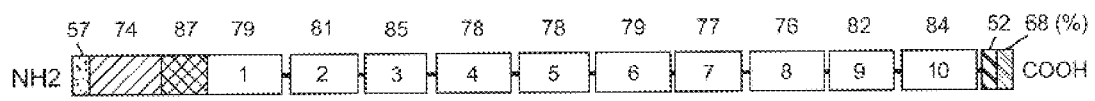
FIG. 3 shows protein similarity between human and mouse DEC-205.
Figure 3A-1:
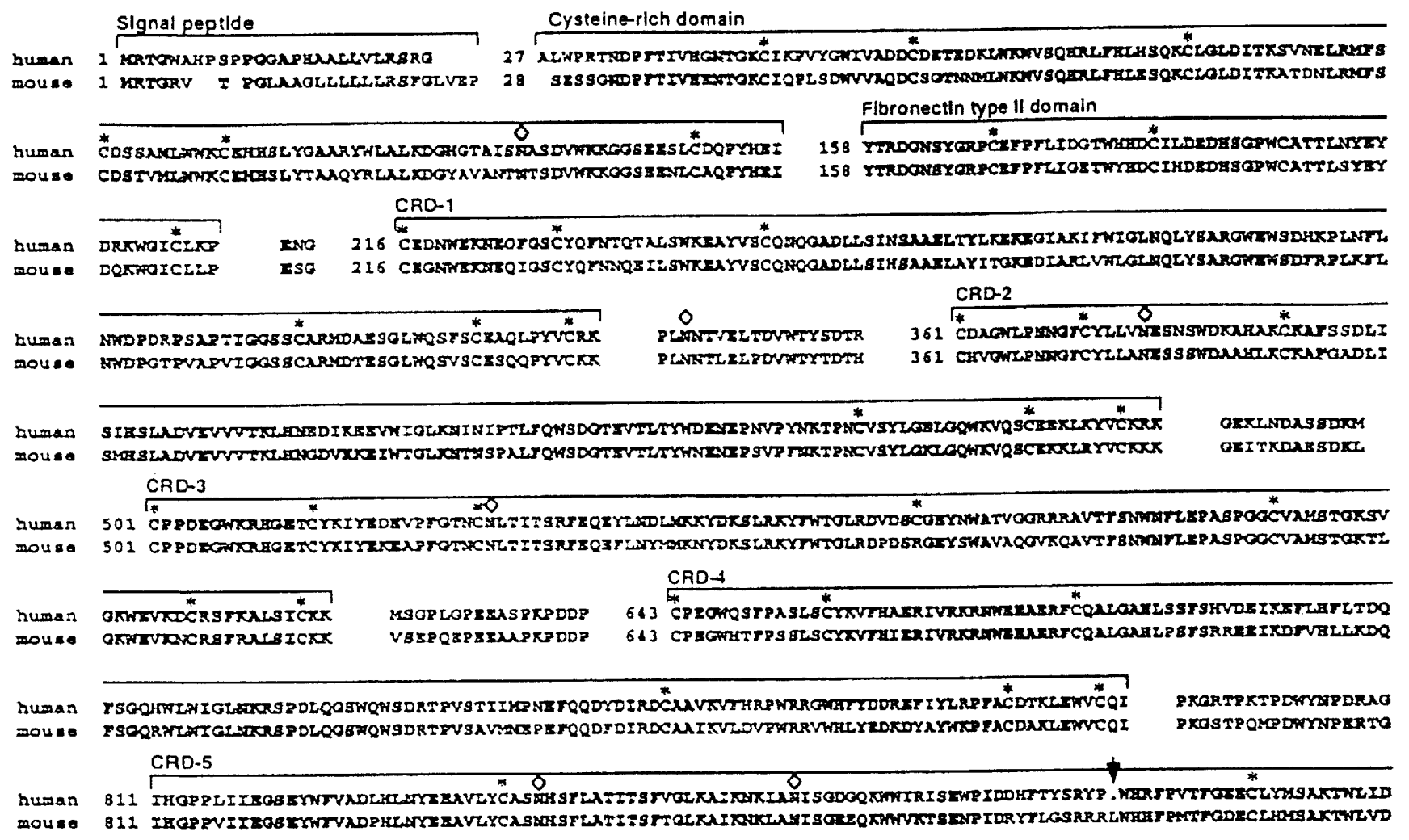
Figure 3A-2:
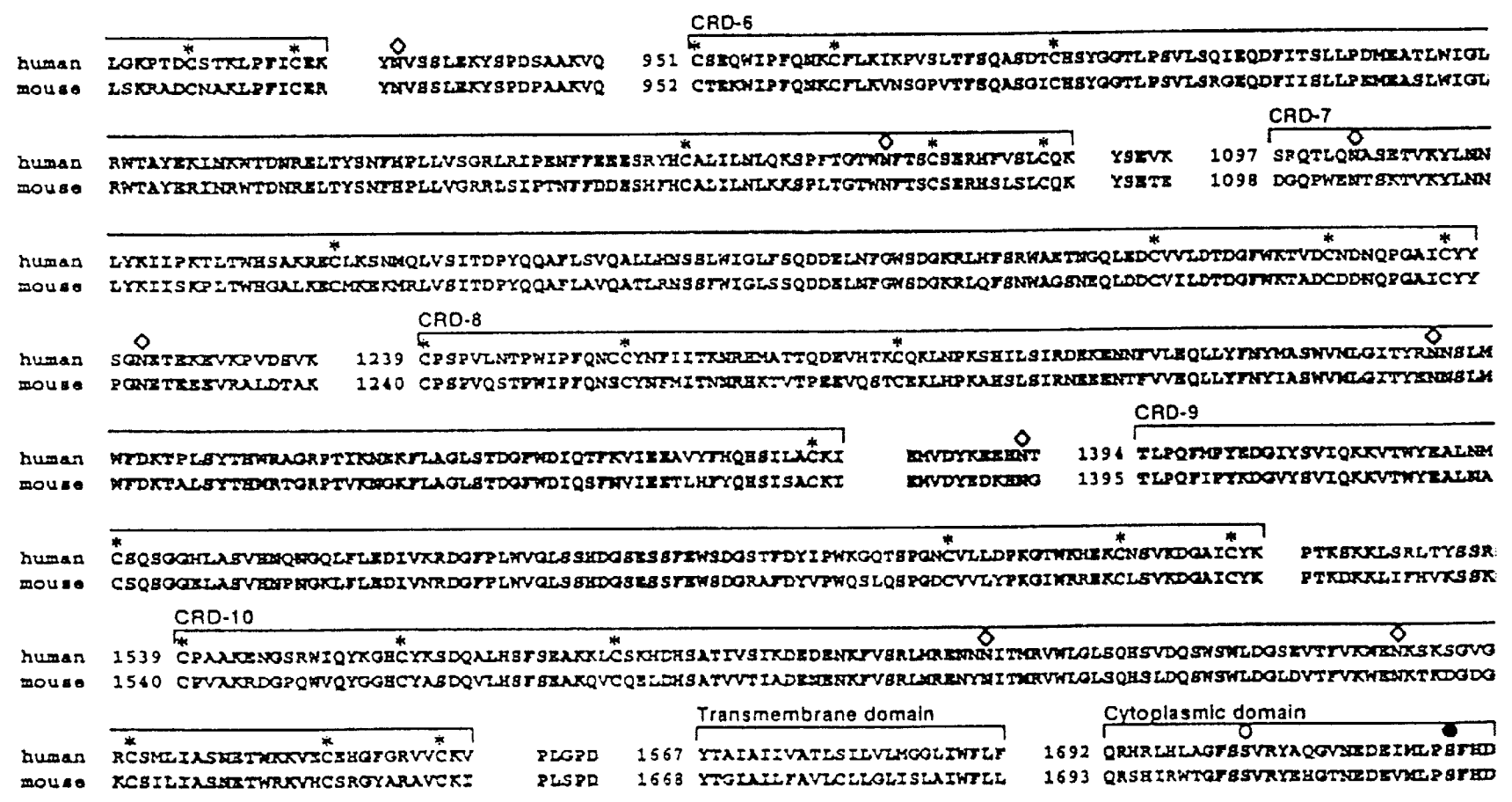

The deduced amino acid sequence of human DEC-205 showed 77% overall identity with the homologous mouse protein (FIG. 3A). All the cysteines, and putative N-glycosylation sites in the extracellular domain of mouse DEC-205, were conserved in the human sequence. In the cytoplasmic domain the putative serine phosphorylation sites by protein kinase C or casein kinase, and a tyrosine, which appears to be important for coated pit-mediated internalization (Ezekowitz, R. A. B., Sastry, K., Bailly, P., and Warner, A. (1990) *J. Exp. Med.* 172, 1785–1794; and Zvaritch, E., Lambeau, G., and Lazdunski, M. (1996) *J. Biol. Chem.* 271, 250–257), were also conserved. There was one amino acid deletion within the CRD-5 in human DEC-205. All the extracelluar domains, including the cysteine-rich domain, fibronectin type II domain, and CRD1–10 were 74–87% identical between human and mouse sequences (FIG. 3B), suggesting the importance of these domains for the function of DEC-205. In contrast, the two hydrophobic domains, including the signal peptide and transmembrane domain, showed much lower identity (57% and 52%, respectively (FIG. 3B)) with the mouse protein, confirming the observation that these hydrohobic domains are more variable, and rapidly evolved structures (Von Heijne, G. (1990) *J. Membrane Biol.* 115, 195–201).

DEC-205 is a Single Copy Gene with Polymorphism—Peripheral blood-derived genomic DNA from 4 individuals was restriction enzyme-digested with BglII, BamHI, HindIII or EcoRI, and subjected to Southern blot analysis. The cysteine-rich domain of the macrophage mannose receptor (Kim, S. J., Ruiz, N., Bezouska, K, and Drickamer, K. (1992) Genomics 14, 721–727; and Harris, N., Peters, L. L., Eicher, E. M., Rits, M., Raspberry, D., Eichbaum, Q. G., Super, M., and Ezekowitz, R. A. B. (1994) *Biochem. Biophys. Res. Com.* 198, 682–692) and phospholipase A2 receptor (Ancian, P., Lambeau, G., Mattei, M. G., and Lazdunski, M. (1995) 270, 8963–8970) is encoded by one exon. Therefore, we amplified the cysteine-rich domain of human DEC-205 using primers 058 and 059 as a potential single exon probe (450 bp), and used this to probe the Southern blot in high stringency. A single band appeared in BglII-, BamHI- or HindIII-digested genomic DNA from all individuals, indicating that DEC-205 is a single copy gene (FIG. 4). The EcoRI digests, however, produced a single band in two individuals and double bands in another, indicating that the DEC-205 gene is polymorphic. Further Southern blot analysis with larger panel of individuals showed identical results (data not shown). Therefore, DEC-205 is a single copy gene with at least one polymorphic site.

DEC-205 Gene Maps to Chromosome Band 2q24-In order to map the human DEC—205 gene, a somatic cell hybrid panel Southern blot (PstI-digested) was probed with the [$^{32}$P]cysteine-rich domain as described above (FIG. 5). A 3.0 kb band in human genomic DNA was found to hybridize strongly, and the identical band appeared in chromosome 2-containing somatic human-mouse hybrid cells, indicating that DEC-205 gene localizes on chromosome 2. The probe also hybridized weakly with hamster DNA, suggesting the presence of DEC-205 homolog in hamster as well as in the mouse (which also hybridized strongly). The origin of the weakly hybridized bands with apparent polymorphism in the human DNA-containing lanes is not known. The identical band appeared in chromosome 2, and may either be related to an alternative exon structure for this region of DEC-205 or result from weak cross hybridization to another gene on chromosome 2.

Fluorescent in situ hybridization then was used to map the DEC-205 gene in detail (FIGS. 6A and 6B). The 6.4 kb recombinant PCR fragment (fragment 6) (FIG. 2A) was prepared from fragment 3 and 4, labeled with biotinylated nucleotides, and used as a probe in a high stringency (FIG. 6A). Ninety-one (80%) of a combined total 114 metaphase cells analysed from three experiments showed fluorescent signals on one (27) or both (64) chromosomes 2 in the middle of the long arm, specifically in band q24 (FIG. 6B). High resolution banding analysis provided a more precise location of signals (not shown). No additional site-specific signals were detected on any other chromosome.

DEC-205 Exhibits Multiple Transcripts in Cell Lines—A panel of human cell lines, including myeloid, B lymphoid, T lymphoid and Hodgkin's desease-derived cell lines, were analyzed for the expression of DEC-205 transcripts by Northern blot analysis with the [$^{32}$P]fragment 3 as a probe (FIG. 7A and 7B). Two DEC-205 transcripts, 7.8 and 9.5 kb in size, were detected, and the 7.8 kb transcript was the most abundant. The expression level varied between cell lines, however the myeloid cell line THP-1, the B lymphoid cell line Mann and the Hodgkin's desease cell line KMH2 showed the highest level of expression. Even with longer exposure, DEC-205 transcripts were not detectable in K562, KG-1, Monomac and Jurkat cells, suggesting these cells are DEC-205 negative (FIG. 7B). Interestingly all Hodgkin's disease-derived cell lines tested express the transcripts. Semiquantitative RT-PCR studies also support these results (data not shown).

C. Recombinant Expression of Human DEC-205

In yet another aspect, the present invention relates to the recombinant expression of human DEC-205 or of its extracellular domain.

The Polynucleotides that encode human DEC-205 or the extracellular domain of the invention may be inserted into known vectors for use in standard recombinant DNA techniques. Standard recombinant DNA techniques are those such as are described in Sambrook et al.; "Molecular Cloning" 2nd Edition Cold Spring Harbour Laboratory Press (1987) and by Ausubel et al., Eds, "Current Protocols in Molecular Biology" Greene Publishing Associates and Wiley-Interscience, New York (1987).

Vectors for expressing proteins in bacteria, especially *E. coli*, are known. Such vectors include the PATH vectors described by Dieckmann and Tzagoloff in *J. Biol. Chem.* 260, 1513–1520 (1985). These vectors contain DNA sequences that encode anthranilate synthetase (TrpE) followed by a polylinker at the carboxy terminus. Other expression vector systems are based on beta-galactosidase (pGEX); lambda P maltose binding protein (pMAL); and gluthathione S-transferase (pGST)—see *Gene* 67, 31 (1988) and *Peptide Research* 3, 167 (1990).

Vectors useful in yeast and insect cells are available and well known. A suitable example of a yeast vector is the $2\mu$ plasmid.

Suitable vectors for use in mammlian cells are also known. Such vectors include well-known derivatives of SV-40, adenovirus, retrovirus-derived DNA sequences and vectors derived from combination of plasmids and phage DNA.

Further eucaryotic expression vectors are known in the art (e.g. P. J. Southern and P. Berg, *J. Mol. Appl. Genet.* 1, 327–341 (1982); S. Subramani et al, *Mol. Cell. Biol.* 1. 854–864 (1981); R. J. Kaufinann and P. A. Sharp, "Amplification And Expression of Sequences Cotransfected with a Modular Dihydrofolate Reductase Complementary DNA Gene," *J. Mol. Biol.* 159, 601–621 (1982); R. J. Kaufmann and P. A. Sharp, *Mol. Cell. Biol.* 159 601–664 (1982); S. I. Scahill et al, "Expression And Characterization Of The Product Of A Human Imnune Interferon DNA Gene In Chinese Hamster Ovary Cells," *Proc. Natl. Acad. Sci. USA* 80 4654–4659 (1983); G. Urlaub and L. A. Chasin, *Proc. Natl. Acad. Sci. USA* 77, 4216–4220, (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac stem, the trc system, major operator and promoter regions of phage lambda, the control region of fd coat protein, the glycolytic promoters of yeast, e.g. the promoter for 3-phosphoglycerate kinase, the promoters of yeast acid phosphatase, e.g. Pho5, the promoters of the yeast alpha-mating factors, and promoters derived from polyoma, adenovirus, retrovirus, and simian virus, e.g. the early and late promoters or SV40, and other sequences known to control the expression of genes of prokaryotic and eucaryotic cells and their viruses or combinations thereof.

Vectors containing the receptor-encoding DNA and control signals are inserted into a host cell for expression of the receptor. Some useful expression host cells include well-known prokaryotic and eucaryotic cells. Some suitable prokaryotic hosts include, for example, *E. coli.* such as *E. coli* SG-936, *E. coli* HB 101, *E. coli* W3110, *E. coli* X1776, E. coli X2282, E. coli DHT, and E. coli MR01, Pseudomonas, Bacillus, such as *Bacillus subtilis*, and Streptomyces. Suitable eucaryotic cells include yeast and other fungi, insect, animal cells, such as COS cells and CHO cells, human cells and plant cells in tissue culture.

D. Ligands

The invention also includes ligands that bind to human DEC-205 of the invention.

The ligand will usually be an antibody or an antibody binding fragment raised against human DEC-205 or its extracellular domain, or against fragments thereof.

Such antibodies may be polyclonal but are preferably monoclonal. Monoclonal antibodies may be produced by methods known in the art. These methods include the immunological method described by Kohler and Milstein in *Nature* 256, 495–497 (1975) and Campbell in "Monoclonal Antibody Technology, the Production and Characterization of Rodent and Human Hybridomas" in Burdon et al. Eds, Laboratory Techniques in Biochemistry and Molecular Biology, Volume 13, Elsevier Science Publishers, Amsterdam (1985); as well as by the recombinant DNA method described by Huse et al. in *Science* 246 1275–1281 (1989).

In yet another form, the ligand may also be a non-protein, probably carbohydrate containing, molecule that acts as a ligand when it binds to, or otherwise comes into contact with, human DEC-205.

In addition, ligands may be of two fimctional types. The first functional type of ligand is a molecule which binds to human DEC-205 and stimulates it in performing its normal function (a "stimulant ligand"). The second functional type of ligand is a molecule which binds to human DEC-205 and inhibits or prevents it performing its normal function (an "antagonistic ligand").

Both types of ligand will find application in either therapeutic or prophylactic treatments as described below.

Example 3 describes the production of anti-DEC-205 antibodies.

EXAMPLE 3

Production of Anti-DEC-205 Antibodies

A BALB/c mouse was immunized ip/sc with L428 cells and boosted SC with two peptides derived from the DEC-205 cDNA sequence. DEC-205 peptide 1 ATTQDEVHTKC [amino acids at positions 267–277 of SEQ ID NO:1] and DEC-205-peptide 2 TEKEVKPVDSVKC [amino acids at positions 1227–1239 of SEQ ID NO:1] were synthesized by Chiron Mimotopes Pty Ltd (Clayton, Victoria, Australia). After a third immunization with the two DEC-205 peptides sc/ip/IV the mouse was sacrificed and a spleen cell suspension prepared. The spleen cells were fused with the NS-1 myeloma cell line using standard techniques (Hock et al, Immunology 1994;83:573). A hybridoma was subsequently isolated, 2F5, which produced monoclonal antibody binding to the DEC-205-peptide 1 but not the DEC-205-peptide 2 or a third control DEC-205-peptide 3 (KCLGLDITKSVNELR) [amino acids at positions 82–96 of SEQ ID NO:1]. This is shown by FIG. 9.

E. Constructs

The invention also provides constructs. The constructs will generally include antigens against which an immune response is desired but can also include other products to be delivered specifically to dendritic cells. Toxins, such as the ricin A chain are not excluded. The other component of the construct will vary, being either a ligand as described above or at least the extracellular domain of human DEC-205. Both constructs will have the potential to manipulate the immune system of the host.

In the ligand-antigen constructs, ligands which bind to human DEC-205 (usually antibodies, antibody-binding fragments or carbohydrates expressing proteins) can be coupled or otherwise associated with the antigen against which an immune response is desired. An example of such antigens are sugar-coated antigens such as tumour-associated antigens In use, the ligand component binds to human DEC-205 and the dendritic cell is 'primed' with the associated antigen. This 'priming' action will assist in the induction of an immediate immune response against the antigen.

The ligand-antigen construct can take any appropriate form for administration to the dendritic cells. Such forms may differ depending upon whether the therapeutic protocol involves isolation of the patients dendritic cells (so that the priming action can take place in vitro) or whether the construct is to be administered to a patient in vivo.

The construct can be directly administered to a patient for in vivo treatment. It can also be administered in a form which allows the construct to be expressed within the patient.

One example of such a form for administration to a patient in vivo is a live recombinant viral vaccine. Such a vaccine includes a polynucleotide encoding the DEC-205 ligand (or a portion thereof) and the antigen. The vaccine is administered to the patient and, once within the patient, expresses the encoded ligand and antigen to bind to the patients dendritic cells (via human DEC-205).

A number of such live recombinant viral vaccine systems are known. An example of such a system is the *Vaccinia* virus system (U.S. Pat. No. 4,603,112; Brochier el al., *Nature* 354:520 (1991)).

Administration can be via intravenous, intramuscular, subcutaneous, topical, oral, intra nasal, rectal or intracerebroventricular routes, as appropriate.

F. Applications

Human DEC-205, its ligands and the constructs discussed above can be employed therapeutically or prophylactically in accordance with this invention to promote or inhibit any of the known actions of dendritic cells and/or to manipulate the immune system.

Thus, the antagonistic ligands per se have potential application *inter alia* blocking or inhibiting the immune response during transplantation procedures.

Ligands also have application in delivering other products with which they are associated directly to dendritic cells. This can be for therapeutic purposes (where the delivered product is an immunogenic antigen) as discussed above. It can also be to target a toxin (such as the ricin A-chain specifically to dendritic cells to selectively destroy them as part of an immunosuppressive process.

G. The Use of Human DEC-205 to Detect Dendritic Cells in Cell Suspensions on Tissues and to Purify Dendritic Cells Monoclonal antibodies or other ligands binding to DEC-205 may be used to identify or isolate DC for scientific study or therapeutic application. For this application, the antibodies or ligands can be used in conjunction with conventional identification/separation systems. An example of such a system is the avidin-biotin immunoaffinity system available from Cell-Pro Inc, Washington, USA (see U.S. Pat. No. 5,215,927, U.S. Pat. No. 5,225,353, U.S. Pat. No. 5,262,334 and U.S. pat. No. 5,240,856).

This system employs directly or indirectly a biotinylated monoclonal antibody directed against a target cell and a column containing immunobilized avidin and can be readily adapted to extract activated human dendritic cells, in this case from human peripheral blood, using the anti-DEC-205 antibody as follows:

1. A sample of human peripheral blood containing the human dendritic cells is mixed with biotinylated anti-DEC-205 antibody and incubated to allow formation of antibody/human DC complexes.
2. Following incubation, the mixture is introduced into a CellPro continuous-flow imnuunoadsorption column filled with avidin-coated beads, the strong affinity between biotin and avidin causing the biotin-coated antibodies (together with the human DC to which they have bound) to adhere to the avidin-coated beads.
3. After unwanted cells present in the mixture are washed away, captured activated human DC are removed from the column by gentle agitation and are available for use.

Variations on this theme using the anti-DEC-205 antibody as primary antibody (to bind to activated DC) and a biotinylated secondary antibody (to bind to the anti-DEC-205 antibody) can also be employed.

It will be appreciated that before admixture with the anti-DEC-205 antibody in accordance with the above protocol, the human peripheral blood sample should be treated to ensure that the DC the sample contains are activated. This can easily be achieved by, for example, overnight incubation of the sample.

H. Functional Equivalents

The invention includes functional equivalents of human DEC-205, extracellular domains and nucleic acid molecules described above.

Human DEC-205 and its extracellular domain are or include proteins. A protein is considered a functional equivalent of another protein for a specific function if the equivalent protein is immunologically cross-reactive with, and has the same function as, the original protein. The equivalent may, for example, be a fragment of the protein, or a substitution, addition or deletion mutant of the protein.

For example, it is possible to substitute amino acids in a sequence with equivalent amino acids using conventional techniques. Groups of amino acids known normally to be equivalent are:
(a) Ala(A) Ser(S) Thr(T) Pro(P) Gly(G);
(b) Asn(N) Asp(D) Glu(E) Gln(Q);
(c) His(H) Arg(R) Lys(K);
(d) Met(M) Leu(L) Ile(I) Val(V); and
(e) Phe(F) Tyr(Y) Trp(W).

Substitutions, additions and/or deletions in human DEC-205 may be made as long as the resulting equivalent protein is immunologically cross-reactive with, and have the same function as, the native human DEC-205.

The equivalent human DEC-205 will normally have substantially the same amino acid sequence as the native human DEC-205. An amino acid sequence that is substantially the same as another sequence, but that differs from the other sequence by means of one or more substitutions, additions and/or deletions is considered to be an equivalent sequence. Preferably, less than 25%, more preferably less tan 10%, and most preferably less than 5% of the number of amino acid residues in the amino acid sequence of the native human DEC-205 are substituted for, added to, or deleted from.

Equivalent nucleic acid molecules include nucleic acid sequences that encode proteins equivalent to human DEC-205 as defined above. Equivalent nucleic acid molecules also include nucleic acid sequences that, due to the degeneracy of the nucleic acid code, differ from native nucleic acid sequences in ways that do not affect the corresponding amino acid sequences.

Those persons skilled in the art will of course appreciate that the above description is provided by way of example only and that the invention is limited only by the lawful scope of the appended claims.

What is claimed is:

1. An isolated human dendritic cell receptor comprising the amino acid sequence set forth in SEQ ID NO:1.
2. An isolated human dendritic cell receptor according to claim 1 comprising amino acids 27 to 1722 of SEQ ID NO:1.
3. An isolated human dendritic cell receptor according to claim 1 comprising amino acids 27 to 1661 of SEQ ID NO:1.
4. An isolated polynucleotide sequence encoding the human dendritic cell receptor of claim 1 comprising the nucleotide sequence set forth in SEQ ID NO:2 or a nucleotide sequence capable of hybridizing to SEQ ID NO:2 or its complementary form under stringency conditions of a final wash in 0.1×SSC, 0.5 w/v SDS at 65° C.
5. An isolated vector comprising the polynucleotide sequence according to claim 4.
6. A method of producing a recombinant polypeptide comprising amino acid sequences derived from a human dendritic cell receptor, said method comprising culturing cells comprising the polynucleotide sequence according to claim 4 for a time and under conditions sufficient for the polynucleotide sequence to be expressed into said polypeptide and then recovering said polypeptide.

* * * * *